(12) United States Patent
Svendsen et al.

(10) Patent No.: US 7,232,803 B2
(45) Date of Patent: Jun. 19, 2007

(54) ANTIMICROBIAL COMPOUNDS AND FORMULATIONS

(75) Inventors: John Sigurd Svendsen, Kvaløysletta (NO); Bengt Erik Haug, Tromsø (NO); Istvan Marko, B-Louvain-la-Neuve (BE); Øystein Rekdal, Tomasjord (NO); Merete Linchausen Skar, Tromsø (NO); Wenche Stensen, Kvaløysletta (NO); Morten Bøhmer Strøm, Tromsø (NO)

(73) Assignee: Lytix Biopharma AS, Tromso (NO)

( * ) Notice: Subject to any disclaimer, the term of this patent is extended or adjusted under 35 U.S.C. 154(b) by 248 days.

(21) Appl. No.: 10/221,040

(22) PCT Filed: Mar. 9, 2001

(86) PCT No.: PCT/GB01/01035

§ 371 (c)(1),
(2), (4) Date: Feb. 27, 2003

(87) PCT Pub. No.: WO01/66147

PCT Pub. Date: Sep. 13, 2001

(65) Prior Publication Data

US 2003/0195144 A1   Oct. 16, 2003

(30) Foreign Application Priority Data

Mar. 9, 2000 (GB) ................... 0005703.4

(51) Int. Cl.
| A61K 38/03 | (2006.01) |
| A61K 38/05 | (2006.01) |
| A61K 38/06 | (2006.01) |
| A61K 38/07 | (2006.01) |

(52) U.S. Cl. ............... 514/17; 514/18; 514/19; 514/20; 514/419; 514/620

(58) Field of Classification Search ............ None
See application file for complete search history.

(56) References Cited

U.S. PATENT DOCUMENTS

| 5,428,016 A | * | 6/1995 | Tomita et al. ............... 514/15 |
| 5,885,782 A | | 3/1999 | Edwards ..................... 435/7.1 |
| 6,143,795 A | * | 11/2000 | Moschner et al. .......... 514/656 |
| 6,251,869 B1 | * | 6/2001 | Bohanon ..................... 514/20 |
| 2003/0059827 A1 | * | 3/2003 | Gonzalez et al. ........... 435/7.1 |
| 2003/0113768 A1 | * | 6/2003 | Zweig ........................ 435/6 |

FOREIGN PATENT DOCUMENTS

| WO | WO 97/31019 A2 | 8/1997 |
| WO | WO 97/40070 A1 * | 10/1997 |
| WO | WO 97/44481 A1 | 11/1997 |
| WO | WO 99/59616 A1 | 11/1999 |
| WO | WO 00/12541 A2 | 3/2000 |
| WO | WO 00/12542 A2 | 3/2000 |
| WO | WO 01/19852 A2 | 3/2001 |

OTHER PUBLICATIONS

Oh, Jong Eun et al., "Synthesis of Novel Unnatural Amino Acid as a Building Block and Its Incorporation into an Antimicrobial Peptide," *Bioorganic & Medicinal Chemistry*, 1999, pp. 2985-2990, vol. 7, No. 12, Elsevier Science Ltd.

Puyal, Christophe et al., "Design of a short membrane-destabilizing peptide covalently bound to liposomes," *Biochimica et Biophysica Acta*, 1994, pp. 259-266, vol. 1195, No. 2, Elsevier Science Ltd.

Boger, Dale L., et al., "Vancomycin CD and DE Macrocyclization and Atropisomerism Studies," *J. Org. Chem.*, 1999, pp. 70-80, vol. 64. American Chemical Society.

Hagen, Erik A., et al., "Syntheses of Analogs of D-Ala-D-Ala as Potential Inhibitors of Bacterial Cell Wall Biosynthesis," *Acta Chem. Scad. B*, 1984, pp. 5-14, vol. 38, No. 1.

Hammam, A.S., et al., "Synthesis & Biological Activities of Some New Peptide Substituted Carbazoloquinones," *Indian J. Chem.*, Apr. 1982, pp. 348-351, vol. 21B.

* cited by examiner

*Primary Examiner*—Jeffrey Edwin Russel
(74) *Attorney, Agent, or Firm*—Rothwell, Figg, Ernst Manbeck

(57) ABSTRACT

The invention relates to the use of a molecule comprising a backbone of 2 to 35 non-hydrogen atoms in length, having covalently attached thereto at least two bulky and lipophilic groups and having at least one more cationic than anionic moiety, in the manufacture of a medicament for destabilizing microbial cell membranes and the use as a membrane acting antimicrobial agent of a molecule comprising a backbone of 2 to 35 non-hydrogen atoms in length, having covalently attached thereto a super bulky and lipophilic group comprising at least 9 non-hydrogen atoms and having at least two more cationic than anionic moieties and to methods of treatment involving such molecules, in particular peptides including peptide derivatives, and peptidomimetics.

9 Claims, 2 Drawing Sheets

SEQUENCE LISTING

```
<160> NUMBER OF SEQ ID NOS: 63

<210> SEQ ID NO 1
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 1

Trp Arg Trp Arg Trp Arg
1               5

<210> SEQ ID NO 2
<211> LENGTH: 6
<212> TYPE: PRT
<213> ORGANISM: Artificial
<220> FEATURE:
<223> OTHER INFORMATION: membrane acting anti-microbial agent molecule
```

```
<400> SEQUENCE: 2

Arg Arg Arg Trp Trp Trp
1               5

<210> SEQ ID NO 3
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 3

Arg Trp Trp Trp Arg Arg
1               5

<210> SEQ ID NO 4
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 4

Trp Trp Arg Arg Arg Trp
1               5

<210> SEQ ID NO 5
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 5

Arg Trp Arg Trp Arg Trp
1               5

<210> SEQ ID NO 6
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 6

Arg Trp Arg Tyr Arg Trp
1               5

<210> SEQ ID NO 7
<211> LENGTH: 5
<212> TYPE: PRT
<213> ORGANISM: Artificial
<220> FEATURE:
<223> OTHER INFORMATION: membrane acting anti-microbial agent molecule

<400> SEQUENCE: 7

Trp Arg Trp Arg Trp
1               5

<210> SEQ ID NO 8
<211> LENGTH: 5
<212> TYPE: PRT
<213> ORGANISM: Artificial
<220> FEATURE:
<223> OTHER INFORMATION: membrane acting anti-microbial agent molecule
```

```
<400> SEQUENCE: 8

Trp Arg Tyr Arg Trp
1               5

<210> SEQ ID NO 9
<211> LENGTH: 5
<212> TYPE: PRT
<213> ORGANISM: Artificial
<220> FEATURE:
<223> OTHER INFORMATION: membrane acting anti-microbial agent molecule

<400> SEQUENCE: 9

Arg Trp Arg Trp Arg
1               5

<210> SEQ ID NO 10
<211> LENGTH: 5
<212> TYPE: PRT
<213> ORGANISM: Artificial
<220> FEATURE:
<223> OTHER INFORMATION: membrane acting anti-microbial agent molecule

<400> SEQUENCE: 10

Trp Arg Trp Arg Tyr
1               5

<210> SEQ ID NO 11
<211> LENGTH: 4
<212> TYPE: PRT
<213> ORGANISM: Artificial
<220> FEATURE:
<223> OTHER INFORMATION: membrane acting anti-microbial agent molecule

<400> SEQUENCE: 11

Arg Trp Trp Arg
1

<210> SEQ ID NO 12
<211> LENGTH: 4
<212> TYPE: PRT
<213> ORGANISM: Artificial
<220> FEATURE:
<223> OTHER INFORMATION: membrane acting anti-microbial agent molecule

<400> SEQUENCE: 12

Trp Arg Arg Trp
1

<210> SEQ ID NO 13
<211> LENGTH: 4
<212> TYPE: PRT
<213> ORGANISM: Artificial
<220> FEATURE:
<223> OTHER INFORMATION: membrane acting anti-microbial agent molecule

<400> SEQUENCE: 13

Trp Arg Trp Arg
1

<210> SEQ ID NO 14
<211> LENGTH: 3
<212> TYPE: PRT
<213> ORGANISM: Artificial
<220> FEATURE:
<223> OTHER INFORMATION: membrane acting anti-microbial agent molecule

<400> SEQUENCE: 14
```

Trp Arg Trp
1

<210> SEQ ID NO 15
<211> LENGTH: 3
<212> TYPE: PRT
<213> ORGANISM: Artificial
<220> FEATURE:
<223> OTHER INFORMATION: membrane acting anti-microbial agent molecule

<400> SEQUENCE: 15

Arg Trp Arg
1

<210> SEQ ID NO 16
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (1)..(1)
<223> OTHER INFORMATION: t-butoxycarbonyl; amine protecting group
<220> FEATURE:
<221> NAME/KEY: MISC_FEATURE
<222> LOCATION: (4)..(4)
<223> OTHER INFORMATION: benzyl ester group; protecting carboxyl group

<400> SEQUENCE: 16

Arg Trp Arg Trp
1

<210> SEQ ID NO 17
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (4)..(4)
<223> OTHER INFORMATION: benzyl ester group; protecting carboxyl group

<400> SEQUENCE: 17

Arg Trp Arg Trp
1

<210> SEQ ID NO 18
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (1)..(1)
<223> OTHER INFORMATION: t-butoxycarbonyl; amine protecting group
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Trp with a benzyl ester group; protecting
      carboxyl group

<400> SEQUENCE: 18

Arg Trp Xaa Xaa

```
<210> SEQ ID NO 19
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Trp with benzyl ester group; protecting
      carboxyl group

<400> SEQUENCE: 19

Arg Trp Xaa Xaa
1

<210> SEQ ID NO 20
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (1)..(1)
<223> OTHER INFORMATION: t-butoxycarbonyl; amine protecting group
<220> FEATURE:
<221> NAME/KEY: MISC_FEATURE
<222> LOCATION: (4)..(4)
<223> OTHER INFORMATION: methyl ester; carboxyl protecting group

<400> SEQUENCE: 20

Arg Trp Trp Arg
1

<210> SEQ ID NO 21
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (4)..(4)
<223> OTHER INFORMATION: methyl ester; carboxyl protecting group

<400> SEQUENCE: 21

Arg Trp Trp Arg
1

<210> SEQ ID NO 22
<211> LENGTH: 2
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (2)..(2)
<223> OTHER INFORMATION: benzyl ester group; carboxyl protecting group

<400> SEQUENCE: 22

Arg Trp
1
```

```
<210> SEQ ID NO 23
<211> LENGTH: 2
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Trp with benzyl ester group; carboxyl
      protecting group

<400> SEQUENCE: 23

Xaa Xaa
1

<210> SEQ ID NO 24
<211> LENGTH: 2
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (2)..(2)
<223> OTHER INFORMATION: methyl ester; carboxyl protecting group

<400> SEQUENCE: 24

Trp Arg
1

<210> SEQ ID NO 25
<211> LENGTH: 3
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (3)..(3)
<223> OTHER INFORMATION: benzyl ester; carboxyl protecting group

<400> SEQUENCE: 25

Trp Arg Trp
1

<210> SEQ ID NO 26
<211> LENGTH: 3
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Trp with benzyl ester; carboxyl protecting
      group

<400> SEQUENCE: 26
```

```
Xaa Xaa Xaa
1

<210> SEQ ID NO 27
<211> LENGTH: 3
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (3)..(3)
<223> OTHER INFORMATION: benzyl ester; carboxyl protecting group

<400> SEQUENCE: 27

Xaa Arg Trp
1

<210> SEQ ID NO 28
<211> LENGTH: 3
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (3)..(3)
<223> OTHER INFORMATION: methyl ester; carboxyl protecting group

<400> SEQUENCE: 28

Trp Trp Arg
1

<210> SEQ ID NO 29
<211> LENGTH: 3
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (3)..(3)
<223> OTHER INFORMATION: methyl ester; carboxyl protecting group

<400> SEQUENCE: 29

Arg Trp Arg
1

<210> SEQ ID NO 30
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (4)..(4)
<223> OTHER INFORMATION: benzyl ester; carboxyl protecting group

<400> SEQUENCE: 30

Arg Trp Arg Trp
1

<210> SEQ ID NO 31
<211> LENGTH: 4
<212> TYPE: PRT
```

```
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Trp with benzyl ester; carboxyl protecting
      group

<400> SEQUENCE: 31

Arg Trp Xaa Xaa
1

<210> SEQ ID NO 32
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (4)..(4)
<223> OTHER INFORMATION: methyl ester; carboxyl protecting group

<400> SEQUENCE: 32

Arg Trp Trp Arg
1

<210> SEQ ID NO 33
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (4)..(4)
<223> OTHER INFORMATION: benzyl ester; carboxyl protecting group

<400> SEQUENCE: 33

Arg Trp Arg Trp
1

<210> SEQ ID NO 34
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: benzyl ester; carboxyl protecting group
<220> FEATURE:
<221> NAME/KEY: MISC_FEATURE
<222> LOCATION: (4)..(4)
<223> OTHER INFORMATION: D-Trp

<400> SEQUENCE: 34

Arg Trp Xaa Xaa
1

<210> SEQ ID NO 35
```

```
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (2)..(2)
<223> OTHER INFORMATION: 2-naphtylalanine
<220> FEATURE:
<221> NAME/KEY: MISC_FEATURE
<222> LOCATION: (6)..(6)
<223> OTHER INFORMATION: 2-naphtylalanine

<400> SEQUENCE: 35

Arg Xaa Arg Tyr Arg Xaa
1               5

<210> SEQ ID NO 36
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (6)..(6)
<223> OTHER INFORMATION: super bulky Pmc group

<400> SEQUENCE: 36

Ala Ala Trp Trp Arg Arg
1               5

<210> SEQ ID NO 37
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (6)..(6)
<223> OTHER INFORMATION: super bulky Pmc group

<400> SEQUENCE: 37

Arg Arg Ala Ala Trp Trp
1               5

<210> SEQ ID NO 38
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (6)..(6)
<223> OTHER INFORMATION: super bulky Pmc group

<400> SEQUENCE: 38

Ala Trp Arg Trp Arg Ala
1               5

<210> SEQ ID NO 39
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
```

```
<222> LOCATION: (6)..(6)
<223> OTHER INFORMATION: super bulky Pmc group

<400> SEQUENCE: 39

Trp Arg Ala Ala Trp Arg
1               5

<210> SEQ ID NO 40
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (6)..(6)
<223> OTHER INFORMATION: super bulky Pmc group

<400> SEQUENCE: 40

Trp Trp Ala Ala Arg Arg
1               5

<210> SEQ ID NO 41
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 41

Trp Trp Ala Ala Arg Arg
1               5

<210> SEQ ID NO 42
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 42

Ala Ala Trp Trp Arg Arg
1               5

<210> SEQ ID NO 43
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 43

Arg Arg Ala Ala Trp Trp
1               5

<210> SEQ ID NO 44
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 44

Trp Arg Ala Ala Trp Arg
1               5

<210> SEQ ID NO 45
```

```
<211> LENGTH: 6
<212> TYPE: PRT
<213> ORGANISM: Artificial
<220> FEATURE:
<223> OTHER INFORMATION: membrane acting anti-microbial agent molecule

<400> SEQUENCE: 45

Ala Trp Arg Trp Arg Ala
1               5

<210> SEQ ID NO 46
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (1)..(2)
<223> OTHER INFORMATION: biphenylalanine

<400> SEQUENCE: 46

Xaa Xaa Arg Arg
1

<210> SEQ ID NO 47
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (2)..(2)
<223> OTHER INFORMATION: biphenylalanine
<220> FEATURE:
<221> NAME/KEY: MISC_FEATURE
<222> LOCATION: (4)..(4)
<223> OTHER INFORMATION: super bulky Pmc group

<400> SEQUENCE: 47

Trp Xaa Arg Arg
1

<210> SEQ ID NO 48
<211> LENGTH: 4
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (2)..(2)
<223> OTHER INFORMATION: biphenylalanine

<400> SEQUENCE: 48

Trp Xaa Arg Arg
1

<210> SEQ ID NO 49
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (1)..(2)
<223> OTHER INFORMATION: biphenylalanine

<400> SEQUENCE: 49
```

```
Xaa Xaa Arg Arg Ala Ala
1               5

<210> SEQ ID NO 50
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (3)..(4)
<223> OTHER INFORMATION: biphenylalanine

<400> SEQUENCE: 50

Ala Ala Xaa Xaa Arg Arg
1               5

<210> SEQ ID NO 51
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (1)..(2)
<223> OTHER INFORMATION: biphenylalanine

<400> SEQUENCE: 51

Xaa Xaa Ala Ala Arg Arg
1               5

<210> SEQ ID NO 52
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (4)..(4)
<223> OTHER INFORMATION: biphenylalanine

<400> SEQUENCE: 52

Ala Ala Trp Xaa Arg Arg
1               5

<210> SEQ ID NO 53
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (2)..(2)
<223> OTHER INFORMATION: biphenylalanine

<400> SEQUENCE: 53

Trp Xaa Ala Ala Arg Arg
1               5

<210> SEQ ID NO 54
<211> LENGTH: 6
<212> TYPE: PRT
<213> ORGANISM: Artificial
<220> FEATURE:
<223> OTHER INFORMATION: membrane acting anti-microbial agent molecule
```

```
<220> FEATURE:
<221> NAME/KEY: MISC_FEATURE
<222> LOCATION: (2)..(2)
<223> OTHER INFORMATION: biphenylalanine

<400> SEQUENCE: 54

Trp Xaa Arg Arg Ala Ala
1               5

<210> SEQ ID NO 55
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (4)..(4)
<223> OTHER INFORMATION: biphenylalanine
<220> FEATURE:
<221> NAME/KEY: MISC_FEATURE
<222> LOCATION: (6)..(6)
<223> OTHER INFORMATION: super bulky Pmc group

<400> SEQUENCE: 55

Ala Trp Arg Xaa Arg Ala
1               5

<210> SEQ ID NO 56
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (5)..(5)
<223> OTHER INFORMATION: biphenylalanine
<220> FEATURE:
<221> NAME/KEY: MISC_FEATURE
<222> LOCATION: (6)..(6)
<223> OTHER INFORMATION: super bulky Pmc group

<400> SEQUENCE: 56

Ala Ala Trp Arg Xaa Arg
1               5

<210> SEQ ID NO 57
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (6)..(6)
<223> OTHER INFORMATION: super bulky Pmc group

<400> SEQUENCE: 57

Arg Arg Ala Ala Trp Trp
1               5

<210> SEQ ID NO 58
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (3)..(3)
```

```
<223> OTHER INFORMATION: biphenylalanine
<220> FEATURE:
<221> NAME/KEY: MISC_FEATURE
<222> LOCATION: (6)..(6)
<223> OTHER INFORMATION: super bulky Pmc group

<400> SEQUENCE: 58

Trp Arg Xaa Arg Ala Ala
1               5

<210> SEQ ID NO 59
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (6)..(6)
<223> OTHER INFORMATION: biphenylalanine

<400> SEQUENCE: 59

Arg Arg Ala Ala Trp Xaa
1               5

<210> SEQ ID NO 60
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (4)..(4)
<223> OTHER INFORMATION: biphenylalanine

<400> SEQUENCE: 60

Ala Trp Arg Xaa Arg Ala
1               5

<210> SEQ ID NO 61
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (5)..(5)
<223> OTHER INFORMATION: biphenylalanine

<400> SEQUENCE: 61

Trp Arg Ala Ala Xaa Arg
1               5

<210> SEQ ID NO 62
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (3)..(3)
<223> OTHER INFORMATION: biphenylalanine

<400> SEQUENCE: 62

Trp Arg Xaa Arg Ala Ala
1               5
```

```
<210> SEQ ID NO 63
<211> LENGTH: 6
<212> TYPE: PRT
<213> ORGANISM: Artificial
<220> FEATURE:
<223> OTHER INFORMATION: membrane acting anti-microbial agent molecule
<220> FEATURE:
<221> NAME/KEY: MISC_FEATURE
<222> LOCATION: (5)..(5)
<223> OTHER INFORMATION: biphenylalanine

<400> SEQUENCE: 63

Ala Ala Trp Arg Xaa Arg
1               5
```

ANTIMICROBIAL COMPOUNDS AND FORMULATIONS

The present invention relates to bioactive molecules, in particular to small molecules which exhibit antimicrobial activity.

Peptides and their derivatives have long been recognised as therapeutically interesting molecules. A wide variety of organisms use peptides as part of their host defense mechanism. Antimicrobial peptides have been isolated from species as diverse as bacteria and mammals [Lehrer, R. I., Lichtenstein, A. K. and Ganz, T. (1993) Ann. Rev. Immunol. 11, 105-128]. Generally, these peptides have a net positive charge and a propensity to form amphiphilic α-helix or β-sheet structures upon interaction with the outer phospholipid bilayer in bacterial cell membranes [Besalle, R., Gorea, A., Shalit, J., Metger, J. W., Dass, C. Desiderio, D. M. and Fridkin, M. (1993) J. Med. Chem. 36 1203-1209]. In most cases the detailed molecular mechanisms of the antibiotic action are unknown, although some peptides categorised as class L (lytic) peptides are believed to interact with bacterial cell membranes, probably forming ion-channels or pores [Ludtke, S. J., He, K., Heller, W. T., Harroun, T. A., Yang, L. and Huang, H. W. (1996) Biochemistry 35 13723-13728] leading to permeability changes and consequent cell lysis.

Magainins are antibacterial peptides from the skin of the frog *Xenopus laevis* and are classified as class L antibiotics because they specifically lyse bacteria; other peptides such as mastroparans, a bee venom, lack this specificity as they lyse eukaryotic as well as prokaryotic cells and are called Class L Venoms [Tytler, E. M., Anantharamaiah, G. M., Walker, D. E., Mishra, V. K., Palgunachari, M. N. and Segrest, J. P. (1995) Biochemistry 34 4393-4401].

As well as magainins and mastroparans, host defense peptides have been isolated from moths and flies (cecropins) and from Horseshoe crab. The direct action of these host defense peptides to repel predators, for example as venoms, is clear. The search for peptides which exhibit antibiotic effects has lead to the identification of other proteins/peptides which would not be expected to have cytotoxic properties. One of these is lactoferrin, an iron transporter which also shows a weak antibacterial effect.

The majority of known antibacterial peptides comprise 10 or more, typically 20 or more amino acids, this number of amino acid being required in order to provide sufficient length for the peptide, generally in α-helical form, to span the bacterial cell membrane and form a pore. Such a mechanism is the generally accepted way in which the majority of such peptides exert their cytotoxic activity.

Synthesis of the antibacterial peptides of the prior art can be difficult, and typically requires the peptides to be synthesised by bacteria or other organisms which can be cultured and harvested to yield the peptide of interest, additional processing steps after isolation of the direct product of translation are generally required. If active peptides could be identified which were shorter, this would enable economic manufacture by synthesis from the amino acid building blocks or available di- or tri-peptides. In addition, short peptides would offer advantages for biodelivery. There is a growing demand for antibiotics which can be administered without the need for an injection, such as by inhalation and absorption across the blood capillaries of the nasal passages. Thus, an object of the present invention is to provide bioactive, particularly antimicrobial e.g. antibacterial, molecules which are small enough to be synthesised without the need to transfect organisms with nucleic acid encoding for the peptide of interest and which offer a variety of different modes of administration.

The search for novel antibiotics has taken on particular urgency because of the increasing number of bacterial strains which are exhibiting resistance to known and extensively used drugs. Those operating in the fields of medicine as well as agriculture, environmental protection and food safety are constantly requiring new antibacterial agents and may have to treat a given population or site with several different antibacterial agents in order to effectively combat the undesirable bacteria.

All peptides, and this applies even more so to short peptides, are susceptible to enzymatic degradation in the human or animal body. Therefore, peptide derivatives or peptidomimetics which retain or even enhance the biological activity of the basic peptide but have a greater circulating half life would be particularly advantageous and the provision of such compounds constitutes a further object of the present invention. Peptidomimetics and other organic molecules may be readily synthesised in large amounts by non-fermentation methods.

Combinatorial libraries have been used to identify active peptides (Blondelle, S. E. et al. [1994] American Society for Microbiology Vol. 38, No. 10, 2280-2286). While a vast number of peptides can be screened in this way, the reasons behind the activity of one peptide compared to another may not be clear. An anomalous result indicating activity for a particular sequence may encourage research into a class of molecules which as a whole do not represent the best therapeutic candidates. In addition, with combinatorial chemistry it is often difficult to be sure about exactly what compounds have actually been made and laborious testing and analysis is required to confirm identity of manufactured compounds. If one is looking to identify a core active motif which may not be sequence or size dependent, combinatorial techniques are unsuitable. Also, the chemistry used in building up the molecule, typically from monomers must be rather simple, limiting the variety of molecules which can be made.

In the present case, the inventors have sought to investigate what structural components are required in order to provide the desired therapeutic and general antimicrobial activity, while limiting toxicity and enabling relatively straightforward manufacture and flexibility in terms of the routes of administration of the active molecules. The techniques used, rather than an undirected production and analysis of thousands, even millions of molecules, akin to looking for a needle in a haystack, have been based on rational design. The inventors have sought to identify important motifs and those components which are both necessary and sufficient to the provision of molecules with the desirable characteristics discussed above. Such an approach has proved effective and is particularly valuable in enabling identification of the smallest, simplest molecules possible which can be synthesised and are preferably resistant to enzymatic degradation, i.e. are not underivatised peptides.

It has surprisingly been found that small molecules, equivalent to 4 amino acids or less, exhibit good bioactivity provided they possess sufficient bulky and lipophilic and cationic groups. Previously, it had been thought that only larger molecules, typically longer peptides, could exhibit the desired therapeutic activity, as a result of the way such molecules were believed to exert their effect on cell membranes. It is particularly surprising that these small molecules exhibit good selectivity, i.e. they are cytotoxic against microbes but have very little, if any, toxic activity against host eurkaryotic cells.

Thus, according to one aspect of the present invention is provided a bioactive molecule comprising a backbone of 2 to 35, typically 4 to 35, preferably 4 to 20, more preferably 4 to 12, e.g. 6 to 9 non-hydrogen atoms in length, having covalently attached thereto at least two bulky and lipophilic groups and having at least one more cationic than anionic moiety for use in therapy, e.g. as an antimicrobial, particularly as an antibacterial agent.

This definition could encompass short unmodified peptides but such peptides which only contain amino acids selected from the 20 genetically coded amino acids and also have no bulky or lipophilic N or C terminal modifications are not included within the scope of this aspect of the present invention. The purpose of the present invention is not to identify active peptide fragments per se but to provide stable active molecules which can be prepared by chemical synthesis.

Such antimicrobial molecules also have non-therapeutic uses, for example in agriculture or in domestic or industrial situations as sterilising agents for materials susceptible to microbial contamination. Thus, in a further aspect, the present invention provides the use of a bioactive molecule comprising a backbone of 2 to 35, typically 4 to 35, preferably 4 to 20, more preferably 4 to 12, e.g. 6 to 9 non-hydrogen atoms in length, having covalently attached thereto at least two bulky and lipophilic groups and having at least one more cationic than anionic moiety as an antimicrobial, particularly as an antibacterial agent.

The molecules exhibit antimicrobial activity, in particular they exert a cytotoxic effect through a direct membrane-affecting mechanism and can be termed membrane acting antimicrobial agents. These molecules are lytic, destabilising or even perforating the cell membrane. This offers a distinct therapeutic advantage over agents which act on or intereact with proteinaceous components of the target cells, e.g. cell surface receptors. While mutations may result in new forms of the target proteins leading to antibiotic resistance, it is much less likely that radical changes to the lipid membranes could occur to prevent the cytotoxic effect. The lytic effect causes very rapid cell death and thus has the advantage of killing bacteria before they have a chance to multiply. In addition, the molecules may have other useful properties which kill or harm the target microbes e.g. an ability to inhibit protein synthesis, thus they may have multi-target activity.

Thus, the invention also provides the use of a bioactive molecule comprising a backbone of 2 to 35, typically 4 to 35, preferably 4 to 20, more preferably 4 to 12, e.g. 6 to 9 non-hydrogen atoms in length, having covalently attached thereto at least two bulky and lipophilic groups and having at least one more cationic than anionic moiety in the manufacture of a medicament having a membrane acting antimicrobial activity. This mode of action means, that while the molecules of the invention may be administered in conjunction with other active antimicrobial agents as part of a combined therapy, they may also be administered on their own, i.e. as the sole antimicrobial agent in a therapeutic regimen. This can be contrasted, for example, with molecules acting as efflux pump inhibitors which are co-administered with a primary antimicrobial agent, often having no antimicrobial activity of their own.

Thus in a preferred embodiment of the invention is provided the use of the molecules defined herein in the manufacture of a medicament for destabilising and/or permeabilising microbial cell membranes. In other words the molecules are provided for use in the destabilisation of microbial cell membranes. By 'destabilisation' is meant a perturbation of the normal three dimensional lipid bi-layer configuration including but not limited to membrane thinning, increased membrane permeability (typically not involving channels) of water, ions or metabolites etc. which also impairs the respiratory systems of the bacteria. The mechanisms for bacterial lysis caused by antimicrobial peptides are extensively reviewed by Sitaram and Nagaraj (N. Sitaram and R. Nagaraj, Biochim. Biphys. Acta vol 1462 1999 p. 29-54) and Shai (Y. Shai, Biochim. Biophys. Acta vol 1462 1999 p. 55-70). Destabilisation kills or weakens the cell making it less likely to grow or reproduce.

As discussed above, the inventors in this case have sought to identify those functional and structural motifs which together give the molecules the desired properties of therapeutic (antimicrobial) activity but low toxicity. In a preferred embodiment of the present invention, a third type of group is also found in the molecules, the first two being positively charged groups and bulky and lipophilic groups. This third group is a carbonyl or similar polar group such as a sulphone, thio carbonyl or imine. Such a group is a hydrogen bond acceptor moiety and may conveniently be found as part of the backbone of the molecule, for example the amide bonds found in peptide or other backbones, other backbones may comprise ester or thioester linkages which give the desired polarity to the molecule.

The 'length' of the backbone is the shortest distance in terms of number of atoms between the two atoms in the backbone which are furthest apart. The two atoms which are furthest apart are those which are separated from each other by the greatest number of covalent bonds. Thus, if to get from one of the two atoms which are furthest apart to the other it is necessary to pass through 6 further atoms, the backbone is 8 atoms in length. Hydrogen atoms are not considered to be atoms of the backbone which will typically comprise carbon, nitrogen or oxygen, possibly sulphur or phosphorous atoms. The backbone may be linear, branched, cyclic or polycyclic.

The backbone may contain one or more cyclic groups but the bulky and lipophilic groups defined herein are not considered to form part of the backbone. The backbone is generally characterised by forming a non-interrupted chain of atoms, including chains forming a closed ring or rings, to which the bulky and lipophilic and cationic groups are attached. By 'non-interrupted' it is meant that the backbone is continuous, with the bulky and lipophilic groups attached thereto rather than interrupting the chain of backbone atoms. Preferably, the atoms of the backbone will form a linear or branched chain.

Thus the following molecule would have a backbone of 8 atoms in length, following the method for calculating backbone length defined above.

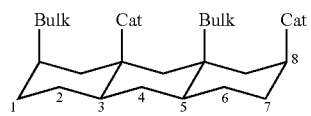

The following molecule would also have a backbone of 8 atoms; as discussed below atoms forming cationic moieties may be part of the backbone.

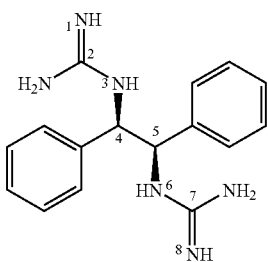

The backbone will typically only comprise less than 4 atoms when one or more of the bulky and lipophilic groups is attached directly to the backbone so that a single atom is part of a defined bulky and lipophilic group as well as the backbone. When an atom is shared in this way, this atom is functionally part of the bulky and lipophilic group and is not counted as an atom of the backbone. Such a molecule is shown below; this molecule thus has a 2 atom backbone.

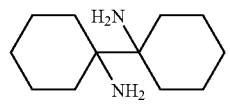

By 'bulky and lipophilic' group is meant an uncharged group of at least 4, preferably at least 5, more preferably at least 6 non-hydrogen atoms, typically incorporating at least one closed ring system. For convenience, such groups are sometimes referred to herein simply as 'bulky' groups. One or more of the bulky and lipophilic groups present in the molecule may have 2 or more closed rings of 5 or 6 atoms and conveniently 2 or more of these rings are fused or bridged. Preferably, at least one of the bulky and lipophilic groups is not provided by the unmodified R group of one of the 20 genetically coded amino acids. Aromatic bulky and lipophilic groups are preferred, as are groups which are three dimensional in character. If the group does not contain one or more rings then it will preferably be branched.

It appears that the positioning of the functional groups (e.g. charged or bulky groups) is not of great importance. The bulky and lipophilic groups have a combined impact on the activity of the molecule as a whole. Thus a comparatively small group together with a rather large group may contribute a similar activity to 2 moderately sized bulky groups. Thus while an example of the minimum bulk present in the molecule is 2 tert.-butyl groups, if one such or similarly sized group is present, a second larger bulky group will preferably be incorporated.

A preferred lower limit of bulk for the molecules defined herein is therefore a tert.-butyl group or equivalent (trimethylsilyl for example is only slightly larger) and a 6-membered ring, e.g. a cyclohexyl or phenyl group. A hierarchy of bulky groups can be exemplified by the following list of amino acid, starting with the least bulky and active: tert.-butylglycine, phenylalanine, cyclohexylalanine, tryptophan, tert.-butylphenylalanine, biphenylalanine and the most bulky and active, tri tert.-butyltryptophan. The skilled reader will appreciate that such groups are given as examples of different sizes and other groups of a similar volume may be used as a substitute without significantly affecting the molecule's activity.

Preferably the molecule will incorporate two groups the size of a phenyl group or larger, i.e. 6-membered rings or equivalent (e.g. —$CH_2C(CH_3)_3$). Particularly preferably, one bulky group is a phenyl group (or equivalent) or larger i.e. has 6 or more non-hydrogen atoms and the other has 9 or more non-hydrogen atoms, e.g. as provided by the R group of tryptophan, tert.-butylphenylalanine or biphenylalanine having 10, 11 and 13 non-hydrogen atoms respectively. It should be remembered that the necessary number and nature of the molecule's bulky groups will vary from one type of microorganism to another, with a given molecule generally much more active against Gram-positive than Gram-negative bacteria.

By a 'cationic moiety' is meant a moiety which has a net positive charge at pH 7.0 or a precursor of such a moiety which is capable of providing in physiological conditions a moiety which has a net positive charge at pH 7.0. Such precursor moieties being known in the art. Likewise an 'anionic moiety' is one which has a net negative charge at pH 7.0 or a precursor thereof. Positive charges are important for attraction to and interaction with the negatively charged phospholipids which make up cell membranes. Suitable chemical groups which provide this cationic functionality include those which comprise an ammonium, guanidino, imidazolium, sulphonium or phosphonium moiety or a tetrazole.

A cationic moiety may be incorporated as part of a bulky and lipophilic group, e.g. a modified tryptophan residue such as 5'-aminoethyltryptophan (available as side chain Boc and N-alpha FMOC derivative from RSP Amino Acids Analogues Inc, Boston, Mass., USA). The atom which actually carries the positive charge when the molecule is at pH 7.0 may be spaced from the backbone. For example, consider the R group of arginine, here the whole R group is considered to be the cationic moiety and the atoms attaching the guanidino group to the α carbon atom are thus considered to be part of the cationic moiety and not part of the backbone.

By way of example, the molecule Arg-Trp OBz, a dipeptide whose C terminus has been modified by formation of a benzoyl ester has one cationic moiety supplied by the R group of arginine and one at the free N terminus. The anionic C terminus has been modified, thus the molecule has two more cationic moieties than anionic moieties, i.e. 2 additional cationic moieties. Likewise, if the N terminus had been modified, for example, by a cyclohexylcarboxylate group, then a cationic moiety would have been 'lost'.

A group which is responsible for increasing the cationicity of the molecule through modification of the C terminus may also provide one of the bulky and lipophilic groups, as in the above example.

A nitrogen atom, for example one which forms part of a cationic ammonium group at the N terminus of a peptide may be one of the backbone atoms. Thus the cationic moieties may form part of the backbone or be appended thereto.

The molecules for use according to the invention will typically have one or more, preferably 2 or more cationic moieties but it is important to consider the number of both cationic and anionic moieties present. For example the tri-peptide Trp-Arg-Trp has two cationic moieties, one supplied by the R group of arginine and the N terminal group. However the anionic C terminus is not modified so the molecule as a whole has only one more cationic moiety than anionic moiety.

Throughout the text, the well known 3 letter and 1 letter codes for the genetically coded amino acids are used.

Preferably, the bioactive molecules of the invention will comprise two or more bulky and lipophilic groups and two or more additional cationic moieties (additional being used to indicate the number of extra cationic moieties present in the molecule as compared to anionic moieties). The inventors have identified the presence of two additional cationic moieties and two bulky and lipophilic groups as one motif which provides particularly active molecules, although further bulky and/or cationic groups may also be present.

Alternatively, molecules incorporating at least three bulky and lipophilic groups and at least one additional cationic moiety, e.g. three bulky and lipophilic groups and one additional cationic moiety, have also been shown to possess good activity and this is a further particularly preferred motif. Cationicity or bulk alone do not provide the desired activity. Similarly, three additional cationic moieties in a molecule with just one bulky and lipophilic group does not provide the desired level of bioactivity, unless the bulky and lipophilic residue is 'super' bulky and lipophilic.

Without wishing to be bound by theory, it seems that the 'super bulky and lipophilic group' is exerting the same influence on the molecule as two regular bulky and lipophilic group. By 'super bulky and lipophilic group' is meant a group of at least 9, typically at least 10 or 11, preferably at least 12 or 13, more preferably at least 15 or 18 non-hydrogen atoms which comprises 1 or more, preferably 2 or more closed ring systems of 4 or more non-hydrogen atoms each, e.g. the R group of tri-tert.butyl tryptophan, di-tert-butyl tryptophan or PMC (2,2,5,7,8-pentamethylchroman-6-sulphonyl) modified tryptophan or adamantylalanine. The super bulky group preferably comprises at least the equivalent of one 6 membered ring attached to a tert.-butyl group e.g. a tert.-butylphenyl group. More preferred are groups comprising two fused or more particularly non-fused 5 or 6 membered rings, e.g. naphtyl, diphenylmethyl, biphenyl or larger groups.

Thus, in a further aspect, the present invention provides a bioactive molecule comprising a backbone of 2 to 35, typically 4 to 35, preferably 4 to 20, more preferably 4 to 12, e.g. 6 to 9 non-hydrogen atoms in length, having covalently attached thereto at least one super bulky and lipophilic group and comprising at least two more cationic than anionic moieties for use in therapy, e.g. as an antimicrobial, as an particularly antibacterial agent. As before, these molecules are membrane acting antimicrobial agents.

Further aspects of the invention include the use as non-therapeutic agents of these molecules; suitable non-therapeutic uses which utilise the general antimicrobial activity of these molecules are discussed herein.

These molecules may also comprise one or more regular bulky and lipophilic groups as described above, covalently attached to the backbone.

Preferred amongst the bioactive molecules described above are peptides which incorporate 1-4 amino acids, preferably 2 or 3 amino acids but also conveniently 4 amino acids. The amino acids may be genetically coded amino acids, genetically coded amino acids which have been modified or modified or non-modified non-genetically coded amino acids which may or may not be naturally occurring. β and γ amino acids as well as α amino acids are included within the term 'amino acids'. Peptides may be cyclic in nature. The term 'peptide' includes depsi peptides.

Typically these peptide or peptide derived molecules will incorporate N- and/or C-terminal modifying groups. The bulky and lipophilic groups may be provided by the R groups of the amino acid residues and/or be part of the N- or C-terminal modifying group. The cationic moieties may be free N-terminal groups, amino acid R groups or part of the N or C terminal modifying groups. The C-terminus is preferably modified, e.g. amidated or more preferably esterified. The use of the term amino acid 'R group' is well understood in the art and used consistently throughout the text to refer to the variable group attached to the α-carbon atom, e.g. for alanine a methyl group.

Thus, a preferred type of backbone for the bioactive molecules described herein will be peptidic or peptide like. Peptidic backbones are characterised by the

NH linkage, a peptide or amide bond. Peptide backbones incorporate at least one such peptide bond. Backbones which terminate in a peptide bond, e.g. an amidated carboxy group are not considered peptidic purely on the basis of this group. Thus, to be classed as peptidic, the backbone must have one or more internal peptide bonds.

While a peptidic backbone is characterised by one or more internal peptide bonds, a peptide will have peptide bonds linking each amino acid residue.

Thus, a compound wherein one or more amide bond has been replaced by an alternative linker but wherein at least one amide bond remains will have a peptidic backbone as defined herein but the compound as a whole will not be a peptide but a peptidomimetic.

Peptide-like (peptidomimetic) backbones are a further class of suitable backbones and may be preferred, for example because they can offer the molecule as a whole resistance to hydrolytic enzymes. Peptidomimetic backbones will generally be linear or linear strings of fused cyclic groups which mimic the peptide backbone.

A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of prior art techniques for the design and synthesis of peptidomimetics. In the present case, where the molecule is reacting with a membrane rather than the specific active site of an enzyme, some of the problems described of exactly mimicing affinity and efficacy or substrate function are not relevant and a peptidomimetic can be readily prepared based on a given peptide structure or a motif of required functional groups. Suitable amide bond surrogates include the following groups: N-alkylation (Schmidt, R. et. al., Int. J. Peptide Protein Res., 1995, 46,47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

The peptidomimetic compounds of the present invention may have one or more, preferably 2 or 3 identifiable sub-units which are approximately equivalent in size and function to amino acids. The term 'amino acid' may thus conveniently be used herein to refer to the equivalent sub-units of a peptidomimetic compound. Moreover, peptidomimetics may have groups equivalent to the R groups of amino acids and discussion herein of suitable R groups, including modified R groups and of N and C terminal modifying groups applies, mutatis mutandis, to peptidomimetic compounds.

As is discussed in the text book referenced above, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Peptidomimetics and thus peptidomimetic backbones wherein the amide bonds have been replaced as discussed above are, however, preferred.

Suitable peptidomimetics include reduced peptides where the amide bond has been reduced to a methylene amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA(1994) 91, 11138-11142. Strongly basic conditions will favour N-methylation over O-methylation and result in methylation of some or all of the nitrogen atoms in the peptide bonds and the N-terminal nitrogen.

Preferred peptidomimetic backbones include polyesters, polyamines and derivatives thereof as well as substituted alkanes and alkenes. The peptidomimetics will preferably have N and C terminii which may be modified as discussed herein.

Peptides and peptidomimetics will generally have a backbone of 4 to 20, preferably 7 to 16 atoms in length. Molecules having backbones at the upper end of these ranges will generally comprise β and/or γ amino acids or their equivalents.

Typically, the peptides for use as antimicrobial agents according to the invention will include 2 or 3 amino acids, at least one of which has a cationic R group. Suitable genetically coded amino acids which provide this cationic functionality would therefore be lysine, arginine and histidine, non-genetically coded amino acids and modified amino acids which also provide a cationic R group include analogues of lysine, arginine and histidine such as homolysine, ornithine, diaminobutyric acid, diaminopimelic acid, diaminopropionic acid and homoarginine as well as trimethyllysine and trimethylornithine.

One or more of the amino acid residues may have an R group which provides one of the required bulky and lipophilic groups. Of the genetically coded amino acids, tryptophan, phenylalanine and tyrosine are particularly suitable and leucine, isoleucine and methionine may also be used. Tryptophan, because of its two fused ring structure and additional bulk is particularly preferred, although the polarity of tyrosine may also be useful. Non-genetic amino acids, which may be naturally occurring, and tryptophan, phenylalanine and tyrosine analogues and amino acids which have been modified to incorporate a bulky and lipophilic R group may also be used. All such modified and unmodified amino acids may conveniently be referred to as 'bulky and lipophilic amino acids'.

The closed ring systems are typically formed of carbon atoms, optionally also including nitrogen, oxygen or sulphur atoms. Particularly preferred amino acids comprise a substituted or unsubstituted indole. The R group may preferably be three-dimensional. Preferred amino acids incorporating a bulky and lipophilic R group include adamantylalanine, 3-benzothienylalanine, 4,4'-biphenylalanine, 3,3-diphenylalanine, homophenylalanine, 2,6-dichlorobenzyltyrosine, cyclohexyltyrosine, 7-benzyloxytryptophan, tri-tert.-butyltryptophan, homotryptophan, 3-(-anthracenyl)-L-alanine, L-p-iso-propylphenylalanine, L-thyroxine, 3,3',5-triiodo-L-thyronine, triiodo-tyrosine.

A lipophilic molecule is one which associates with its own kind in an aqueous solution, not necessarily because the interactions between the lipophilic molecules are stronger than between the lipophilic molecule and water but because interactions between a lipophilic molecule and water would destroy the much stronger interactions between the water molecules themselves. It is therefore preferable that the bulky and lipophilic R group should not contain many polar functional groups e.g. no more than 4, preferably 2 or less. Such groups would increase the binding interaction with the aqueous surroundings and hence lower the lipophilicity of the molecule. For example, a phenyl group as a component of a bulky and lipophilic group may be preferred to a pyridyl group, even though they have the same number of non-hydrogen atoms and are of a similar overall size. However, the presence of a hydroxyl group in a bulky and lipophilic group has been shown to enhance activity and particularly in longer peptide and peptidomimetic compounds, one or more of the bulky and lipophilic groups will preferably contain one or two polar groups, particularly hydroxy groups. Thus amphipathic groups such as phenolic groups may be particularly effective bulky and lipophilic groups, especially in longer molecules.

Non-genetic bulky and lipophilic amino acids include modified tryptophan, tyrosine and phenylalanine residues, in particular tryptophan residues which have been substituted at the 1-, 2-, 5- and/or 7-position of the indole ring, positions 1- or 2- being preferred e.g. 5' hydroxy tryptophan. A variety of other amino acid derivatives having a bulky and lipophilic character are known to the man skilled in the art.

Suitable amino acids include thyroxine and the following commercially available amino acids and their derivatives: L-3-benzothienylalanine, CAS=72120-71-9 (Synthetech), D-3-benzothienylalanine, CAS=111139-55-0 (Synthetech), L-4,4'-biphenylalanine (Synthetech), D-4,4'-biphenylalanine (Synthetech), L-4-bromophenylalanine, CAS=24250-84-8 (Synthetech), D-4-bromophenylalanine, CAS=62561-74-4 (Synthetech), L-2-chlorophenylalanine, CAS=103616-89-3 (Synthetech), D-2-chlorophenylalanine, CAS=80126-50-7 (Synthetech), L-3-chlorophenylalanine, CAS=80126-51-8 (Synthetech), D-3-chlorophenylalanine, CAS=80126-52-9 (Synthetech), L-4-chlorophenylalanine, CAS=14173-39-8 (Synthetech), D-4-chlorophenylalanine, CAS=14091-08-8 (Synthetech), L-3-cyanophenylalanine CAS=57213-48-6 (Synthetech), D-3-cyanophenylalanine (Synthetech), L-4-cyanophenylalanine (Synthetech), D-4-cyanophenylalanine (Synthetech), L-3,4-dichlorophenylalanine, CAS=52794-99-7 (Synthetech), D-3,4-dichlorophenylalanine, CAS=52794-98-6 (Synthetech), L-3,3-diphenylalanine (Synthetech), D-3,3-diphenylalanine (Synthetech), L-homophenylalanine, CAS=943-73-7 (Synthetech), D-homophenylalanine, CAS=82795-51-5 (Synthetech), L-2-indanylglycine (Synthetech), D-2-indanylglycine (Synthetech), L-4-iodophenylalanine, CAS=24250-85-9 (Synthetech), D-4-iodophenylalanine, CAS=62561-75-5 (Synthetech), L-1-naphthylalanine, CAS=55516-54-6 (Synthetech), D-1-naphthylalanine, CAS=78306-92-0 (Synthetech), L-2-Naphthylalanine, CAS=58438-03-2 (Synthetech), D-2-naphthylalanine, CAS=76985-09-6 (Synthetech), L-3-trifluoromethylphenylalanine, CAS=14464-68-7 (Synthetech), D-3-trifluoromethylphenyl-alanine (Synthetech), L-4-trifluoromethylphenylalanine, CAS=114926-38-4 (Synthetech), D-4-trifluoromethyl-phenylalanine, CAS=114872-99-0 (Synthetech), Boc-D-homophenylalanine (Neosystem Laboratoire), Boc-L-homophenylalanine (Neosystem Laboratoire), Fmoc-4-methyl-D-phenylalanine (Neosystem Laboratoire), Fmoc-4-methyl-L-phenylalanine (Neosystem Laboratoire), 2,6-dichlorobenzyltyrosine, CAS=40298-71-3 (Senn Chemicals), Benzyltyrosine Fmoc (Senn Chemicals), Cyclohexyltyrosine Fmoc (Senn Chemicals), L-3,5-diiodotyrosine, CAS=300-39-0 (Senn Chemicals), D-3,5-diiodotyrosine (Senn Chemicals), L-3,5-dibromotyrosine (Senn Chemicals), D-3,5-dibromotyrosine (Senn Chemicals), L-t-butyltyrosine (Senn Chemicals), L-t-butyltyrosine (Senn Chemicals), N-Acetylhomotryptophan (Toronto Research), 7-Benzyloxytryptophan (Toronto Research), Homotryptophan (Toronto Research), 3-(-Anthracenyl)-L-alanine Boc (or Fmoc) (Peninsula Laboratories), 3-(3,5-Dibromo-4-chlorophenyl)-L-alanine (Peninsula Laboratories), 3-(3,5-Dibromo-4-chlorophenyl)-D-alanine (Peninsula Laboratories), 3-(2-Quinoyl)-L-alanine Boc (or Fmoc) (Peninsula Laboratories), 3-(2-Quinoyl)-D-alanine Boc (or Fmoc) (Peninsula Laboratories), 2-Indanyl-L-glycine Boc (Peninsula Laboratories), 2-Indanyl-D-glycine Boc (Peninsula Laboratories), L-p-t-butoxyphenylglycine Fmoc (RSP), L-2-t-butoxyphenylalanine Fmoc (RSP), L-3-t-butoxyphenylalanine Fmoc (RSP), L-homotyrosine, O-t-butyl ether Fmoc (RSP), L-p-t-butoxymethylphenylalanine Fmoc (RSP), L-p-methylphenylalanine Fmoc (RSP), L-p-ethylphenylalanine Fmoc (RSP), L-p-iso-propylphenylalanine Fmoc (RSP), L-p-methoxyphenylalanine Fmoc (RSP), L-p (tBu-thio)phenylalanine Fmoc (RSP), L-p-(Trt-thiomethyl) phenylalanine Fmoc (RSP), L-p-hydroxymethyl-phenylalanine, O-t-butyl (RSP), L-p-benzoylphenylalanine (Advanced ChemTech), D-p-benzoyl-phenylalanine (Advanced ChemTech), O-benzyl-L-homoserine Boc (Advanced ChemTech), O-benzyl-D-homoserine Boc (Advanced ChemTech), L-β-1-Naphthyl-alanine (Advanced ChemTech), D-β-1-Naphthyl-alanine (Advanced ChemTech), L-penta-fluorophenylalanine Boc (Advanced ChemTech), D-penta-fluorophenylalanine Boc (Advanced ChemTech), D-penta-fluorophenylalanine Fmoc (Advanced ChemTech), 3,5-Diiodo-L-tyrosine Fmoc (Boc) (Advanced ChemTech), L-Thyroxine Na, CAS=6106-07-6 (Novabiochem), 3,3',5-Triiodo-L-thyronine Na, CAS=55-06-1 (Novabiochem).

Surprisingly, it has been found that standard chemical protecting groups when attached to an amino acid R group can provide suitable bulky and lipophilic groups. Such modified R groups constitute preferred bulky and lipophilic groups. Suitable amino acid protecting groups are well known in the art and include Pmc (2,2,5,7,8-pentamethyl-chroman-6-sulphonyl), Mtr (4-methoxy-2,3,6-trimethylbenzenesulfonyl) and Pbf (2,2,4,6,7-pentamethyldihydrobenzofuransulfonyl), which may conveniently increase the bulk and lipophilicity of aromatic amino acids, e.g. Phe, Trp and Tyr. Also, the tert.-butyl group is a common protecting group for a wide range of amino acids and is capable of providing bulky and lipophilic groups as described herein, particularly when modifying aromatic residues. The Z-group (carboxybenzyl) is a further protecting group which can be used to provide a bulky and lipophilic group.

A bulky and lipophilic group as defined above may also be provided by an N terminal modifying group. Such bulky and lipophilic N-terminal modifications will preferably comprise a 5- or 6-membered ring which may be alkyl or aryl e.g. cyclohexylcarboxylate or benzylcarboxylate. The bulky and lipophilic N-terminal modifying group may encompass 2 or more fused rings one or more of which may be a 5-membered ring e.g. adamantyl or indole. In addition, due to its tendency to cause unacceptable levels of toxicity (i.e. haemolytic activity) and to provide peptides which are bacteriostatic rather than bactericidal, Fmoc is excluded from possible bulky and lipophilic N terminal modifications. N terminal acetyl groups are not preferred for similar reasons.

Suitable molecules which could be used to modify the N-terminus and provide a bulky and lipophilic group include:

cis-Bicyclo[3.3.0]octan-2-carboxylic acid, [18209-43-3] (Aldrich); Abietic acid, [514-10-3]-(Aldrich); Ursolic acid, [77-52-1] (Aldrich); (1,2-Methanofullerene $C_{60}$)-61-carboxylic acid, [155116-19-1] (Fluka); Dimethyl cubane-1,4-dicarboxylate, [29412-62-2] (Fluka); 2-Norbornaneacetic acid, [1007-01-8] (Aldrich); 4-Pentylbicyclo[2.2.2]octane-1-carboxylic acid, [73152-70-2] (Aldrich); Adamantyl acetic acid; 3-Noradamantanecarboxylic acid, [16200-53-6] (Aldrich); 9-Fluoreneacetic acid, [6284-80-6] (Aldrich); cis-Decahydro-1-naphthol, [36159-47-4] (Aldrich); 9-Ethyl-bicyclo[3.3.1]nonane-9-ol, [21915-33-3] (Aldrich); 3-Quinuclidinol, [1619-34-7] (Aldrich); [[(1S)-endo]-(−)-Borneol, [464-45-9] (Aldrich); (1R,2R,3R,5S)-(−)-Isopinocampheol, [25465-65-0] (Aldrich); Dehydroabietylamine [1446-61-3] (Aldrich); (±)-3-Aminoquinuclidine [6530-09-2] (Aldrich); (R)-(+)-Bornylamine, [32511-34-5] (Aldrich); 1,3,3-Trimethyl-6-aza-bicyclo[3.2.1]octane [53460-46-1] (Aldrich); 1-Adamantylamine, [768-94-5] (Aldrich); 9-Aminofluorene, [5978-75-6] (Aldrich); (1R)-(−)-10-Camphorsulfonic acid, [35963-20-3] (Aldrich); 5-Isoquinolinesulfonic acid, [27655-40-9] (Aldrich); 2-Quinolinethiol, [2637-37-8] (Aldrich); 8-Mercaptomenthone, [38462-22-5] (Aldrich).

N-terminal modifications which provide bulky and lipophilic groups will therefore typically comprise a bulky and lipophilic group "R" which may be attached directly to the N-terminal amine to form a mono-, di- and possibly cationic trialkylated N-terminal amine. Alternatively, the R group may be attached via a linking moiety e.g. a carbonyl group (RCO) e.g. adamantyl or benzyl, carbamate (ROCO), or a linker which forms urea (RNHCO) or ($R_2$NCO) or by a linker which forms a sulfonamide, boronamide or phosphonamide. Sulfonamide forming linkers may be particularly useful when a more stable peptide is required. The bulky and lipophilic group R comprises a preferably saturated cyclic group, more preferably a polycyclic group wherein the cyclic groups are fused or bridged.

A bulky and lipophilic group as defined above may also be provided by a C-terminal modifying group. Suitable C-terminal modifications include the formation of esters, including thioesters or substituted primary and secondary amides to form e.g. a benzyl or cyclohexyl ester or amide. In general, esters are preferred. Other bulky and lipophilic C-terminal groups include naphthylamine and substituted aromatic amines such as phenyl-ethylamine. Standard C-terminal protecting groups may also provide a bulky and lipophilic group.

C-terminal modifications will therefore typically comprise a bulky and lipophilic group "R" which may be attached directly to the C-terminal carboxy group to form a ketone. Alternatively, the R group may be attached via a linking moiety, e.g. (OR) which forms an ester at the C-terminus, (NH—R) or (NR$_2$, wherein the two R groups needs not be the same) which form primary and secondary amide groups respectively at the C-terminus or groups (B—(OR)$_2$) which form boronic esters or phosphorous analogs. Dae (diaminoethyl) is a further linking moiety which may be used to attach a bulky and lipophilic group, e.g. carbobenzoxy (Z) to the C-terminus.

C-terminal modifications have the advantage of 'removing' an anionic group and thus increasing the cationic nature of the molecule as a whole. Therefore, while the cationic N-terminus will generally not be modified unless by a bulky and lipophilic group, the C-terminus will typically be modified either by the incorporation of a bulky and lipophilic group or otherwise to negate the negative charge, e.g. by amidation or formation of a non-bulky and lipophilic ester e.g. an alkyl ester such as a methyl ester. In this way, the peptide Tbt-Arg-Trp-NH$_2$ can have the desirable 2 bulky and lipophilic groups (provided by Tbt and Trp) and 2 cationic groups, at the N-terminus and the R group of arginine, neither of which are 'negated' by an anionic C-terminus.

A moderately bulky C terminal group, such as a group comprising a single, preferably 6-membered, ring such as a group forming a benzyl ester has been shown to provide peptides with particularly good therapeutic properties and peptides comprising such group thus make up a preferred group of molecules according to the present invention.

Thus, according to a further aspect, the present invention provides artificial peptides (peptide derivatives) of 1 to 4 amino acids, typically 2, 3 or 4 amino acids in length which incorporate at least 2 bulky and lipophilic groups (or at least one super bulky and lipophilic group) and have at least one more cationic than anionic moiety. Preferably the peptides incorporate at least 2 bulky and lipophilic groups (or at least 1 super bulky and lipophilic group) and at least two more cationic than anionic moieties or at least 3 bulky and lipophilic groups and at least one more cationic than anionic moiety. The molecules for use according to the invention are preferably peptides, including peptide derivatives or peptidomimetics and they are preferably non-cyclic.

Peptidomimetic equivalents of the above peptides constitute a further aspect of the present invention. Such a peptidomimetic molecule may contain one or more internal amide bonds and the backbone of such a molecule, would as discussed above thus be considered peptidic although as a result of other amide bonds or other modifications, the molecule is not 'a peptide'.

The terms 'bulky and lipophilic', 'super bulky and lipophilic' as well as the definitions of cationic and anionic groups are as described previously. These short peptides will preferably be modified at the N and/or C terminus. The peptides are referred to as 'artificial peptides' to indicate that peptides incorporating only amino acids selected from the 20 genetically coded amino acids and no bulky and lipophilic N or C terminal modification are not intended to be covered within the scope of this aspect of the invention. In addition, as discussed above due to its tendency to cause unacceptable levels of toxicity (i.e. haemolytic activity) Fmoc is excluded from possible bulky and lipophilic N terminal modifications.

There will be practical upper limits on how bulky and lipophilic a group can be particularly in terms of increasing toxicity of the molecule to unacceptable levels. This may be dependent on the overall size of the molecule and factors such as three dimensionality of the group and the total number of non-hydrogen atoms in the group as well as its position within the molecule as a whole, i.e. whether it is a terminal or internal group.

The present invention, as well as providing a group of compounds for use in therapy and novel bioactive molecules per se, also provides a method of drug identification and production based on the functional motifs identified herein. It has surprisingly been found that very small molecules, such as small peptides can have excellent therapeutic, e.g. antimicrobial activity but that such activity is dependent on the presence of a certain number of bulky and lipophilic and cationic moieties; suitable motifs for these functional groups are defined herein. Identification of these motifs provides a very useful strategy for those seeking to prepare antimicrobial molecules and particularly allows the preparation of molecules which are smaller than conventional therapeutic antimicrobial agents. Potential lead candidate drug compounds may be identified, and optionally further modified to enhance activity.

Thus, in a further aspect, the present invention provides a process for the preparation of a membrane acting antimicrobial agent comprising identifying a peptide of 1 to 4 amino acids in length having at least one more cationic than anionic moieties and having at least two bulky and lipophilic groups or groups which could be modified to provide bulky and lipophilic groups and synthesising a derivative or a peptidomimetic of said peptide which has a backbone of 2 to 35, typically 4 to 35, preferably 4 to 20, more preferably 4 to 12, e.g. 6 to 9 non-hydrogen atoms in length, having covalently attached thereto at least two bulky and lipophilic groups and having at least one more cationic than anionic moiety and optionally formulating said peptide, peptide derivative or peptidomimetic with a physiologically acceptable carrier or excipient.

The initially identified molecule may be a peptide such as a fragment of a known peptide or a fragment synthesised de novo. This peptide may be tested for its biological activity and then the synthesizing step performed before testing of the peptide, derivative or peptidomimetic of the invention. Preferably, the initially identified peptide will not be synthesised and tested but will simply provide the basis for synthesis of a molecule according to the present invention. That molecule may itself be tested and then further modified in accordance with the teaching herein. Prior to synthesis, there will be a design process where the precise nature and position of the functional groups and the necessary synthetic steps are determined.

More generally, the present invention provides a process for the preparation of an antimicrobial or antitumoural agent which method comprises identifying a compound comprising a backbone of 2 to 35, typically 4 to 35, preferably 4 to 20, more preferably 4 to 12, e.g. 6 to 9 non-hydrogen atoms in length, having covalently attached thereto at least two bulky and lipophilic groups and having at least one more cationic than anionic moiety and synthesising said compound and optionally formulating said compound with a physiologically acceptable carrier or excipient.

This method also applies to those molecules which comprise only one super bulky and lipophilic group.

It has also been observed that the incorporation of one or more enantiomeric amino acids can significantly increase the bioactivity of the peptides, such peptides would also have reduced susceptibility to enzymatic hydrolysis. Thus one or more of the amino acids present in the molecule may be in the D-form, e.g. all amino acids may be in the D form, alternate residues may be in the D form or there may be blocks of D and L residues.

Suitable compounds which have the structural and functional characteristics of the bioactive molecules of the present invention but which are not peptides or peptidomimetics may be readily prepared by the man skilled in the art. In this case, the 'backbone' typically provides a scaffold onto which the cationic and bulky and lipophilic groups i.e. the functional groups responsible for the molecule's activity are attached. Peptidomimetic molecules are described above and may provide useful therapeutic compounds but the present invention also relates to molecules which are not closely based on a standard peptide structure.

The 'backbone' may be simply a linker moiety which joins the different functional groups together and provides the required spacing to allow the cationic and bulky/lipophilic moieties to perform their roles of attraction to and destabilisation of the cell membrane. Depending on the particular bulky and lipophilic and cationic moieties selected, a certain amount of backbone structure will be required to give the molecule chemical stability, such considerations being very familiar to the man skilled in the art. The backbones of such molecules may be linear, branched, cyclic or polycyclic, aromatic or aliphatic, possibly based on a sugar or sugar derived compound such as a sugar alcohol or amino sugar, aminoglycoside, glycoside, aza sugar, innositol, mannitol, sphingoside or polyester or polyamine.

The backbones will typically comprise carbon, nitrogen, oxygen, sulphur or phosphorous atoms but may be further substituted. Preferably, the backbones will be stable and rather unreactive under normal physiological conditions, resistant to enzymatic cleavage and having few charged or polar groups. The backbone will preferably be biocompatible. These non-peptide like backbones (i.e. not peptide or peptidomimetic) will have a backbone length of 2-35 non-hydrogen atoms and where the backbones are polycyclic e.g. cyclodextrins may actually contain a great many more non-hydrogen atoms. Preferred backbones will be 4 to 24 e.g. 7 to 16 non-hydrogen atoms in length.

From a synthetic point of view, the majority of suitable non-peptide like backbones may conveniently be divided into two classes, a scaffold type backbone, typically a simple molecule which has a sufficient number of appendage points for incorporation of the necessary cationic and bulky and lipophilic moieties. Linear and cyclic sugars, polyols and inositols fall within this category and may be exemplified by mannitol which has had its hydroxy groups modified by the addition of bulky and lipophilic and cationic moieties. Such molecules may also be formed by the reaction of two or more distinct components, e.g. the formation of an ester by the reaction of arginine and mandelic acid. The basic structure or backbone scaffold may be formed in this way and the molecule optionally modified to incorporate further dationic and bulky and lipophilic groups. These scaffold backbones will preferably be cyclic, e.g. a 4-20 membered ring more typically comprising 6-20 e.g. 9-12 non-hydrogen atoms.

The purpose of the scaffold molecule is to present the functional groups e.g. cationic or bulky and lipophilic groups, in a position necessary for bioactivity. The scaffold molecule must therefore be able to constrain the topology of the moieties responsible for the bioactivity. One such suitable scaffold molecule is a highly functionalised small (5-7 membered) ring of defined stereochemistry [Luthman, K. and Hacksell, U., A Textbook of Drug Design and Development, Krogsgaard-Larsen, Liljefors and Madsen (Eds.) Harwood Academic Press (1996) 9, 386]. In order to prepare the final molecule a suitable protected scaffold molecule must be chosen. The synthesis will then typically proceed as follows: first one of the preferred moieties is linked to the scaffold typically by ester, ether, amide or amine bond, the next appendage point in the scaffold molecule is deprotected and connected to the next preferred moiety as described above. The process of deprotection and connection is repeated until the required number of functional groups is obtained. The techniques of protection and deprotection are well known to the man skilled in the art and can also be found in the literature [Greene, T. W. and Wuts, P. G. M., Protective Groups in Organic Synthesis, 2nd ed., John Wiley & Sons, Inc. 1991].

An example of a scaffold molecule and its functionalised analog is shown below.

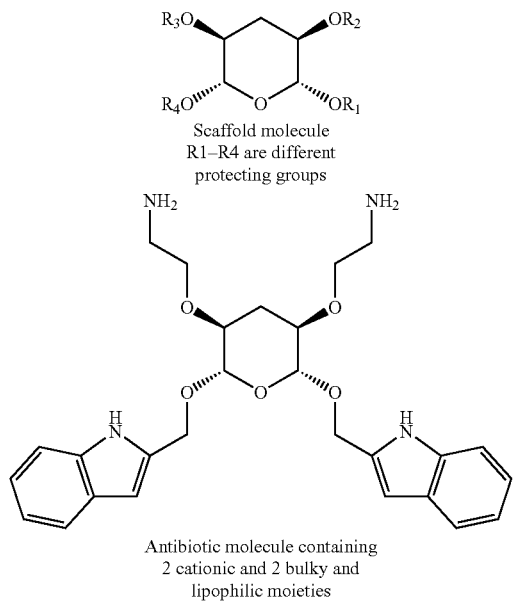

Scaffold molecule
R1–R4 are different protecting groups

Antibiotic molecule containing
2 cationic and 2 bulky and
lipophilic moieties

As well as sugar based scaffold backbones, macrocyclic amines such as tri- and tetraaza macrocyclic amines (e.g. 1,4,7-triazacyclononane and 1,4,7,10-tetraazacyclododecane) are also particularly suitable and are readily derivatised at the N atoms to incorporate the necessary functional moieties as discussed above.

Alternatively, the molecule may be built up from similar monomer sub-units, although such compounds will often be classed as peptidomimetics as discussed above.

Molecules may be constructed using a 'jigsaw' technique of 'interlocking' i.e. reactive subunits which typically each comprise a portion which will form the backbone of the molecule as well as carrying a functional group, i.e. a cationic or bulky and lipophilic moiety. The produced bioactive molecule may be linear comprising a chain of monomer subunit$ or provide a cyclic or polycyclic structure, which may be 3-dimensional. This particularly provides a convenient alternative to decorating a basic scaffold backbone in the synthesis of more complex molecules which do not comprise repeating similar monomer subunits. Such techniques are known in the art.

Suitable bulky and lipophilic groups and cationic moieties are discussed above and a large number of specific examples are given in relation to N and C terminal modifying and amino acid R groups. The same and similar bulky and lipophilic and cationic moieties may be incorporated in the non-peptide like molecules. For non-peptide like molecules particularly suitable bulky and lipophilic groups include.

The bioactive molecules for use according to the invention will preferably combine good activity against target pathogens e.g. as measured by MBC values and comparatively low toxicity as measured by hemolytic activity. Thus the molecules will preferably have an MBC against S. aureus of 50 μg/ml or less, more preferably 20 μg/ml or less and a hemolytic activity of $EC_{50} \geq 500$ μg/ml, preferably $\geq 1000$ μg/ml.

The principles which led to identification of the above described molecules have been used to identify slightly larger bioactive molecules, based on peptides of 5 or 6 amino acids in length. Here the motif of bulky and lipophilic and cationic moieties identified which provides good activity is at least 2 bulky and lipophilic groups, preferably 3 such groups and at least 2 cationic moieties, preferably 3 or 4 such moieties. Suitable bulky and lipophilic and cationic moieties are as defined above in relation to the smaller molecules.

These peptides are further characterised in that at least one of the bulky and lipophilic or cationic moieties is not provided by a genetically coded bulky and lipophilic or cationic amino acid such as tryptophan, phenylalanine, tyrosine, arginine, lysine or histidine. Thus, this moiety, which is conveniently referred to herein as an 'artificial bulky and lipophilic moiety' or 'artificial cationic moiety' may be provided by the R group of a non-genetically coded bulky and lipophilic amino acid such as tri-tert.-butyl tryptophan or by the R group of a non-genetically coded cationic amino acid such as homoarginine. Suitable non-genetically coded amino acids may be naturally occurring or synthetic and are exemplified herein in relation to the smaller molecules. An artificial bulky and lipophilic moiety may also conveniently be provided by modification of the R group of a genetically coded or non-genetically coded amino acid, e.g. with PMC or another protecting group. The modified amino acid may itself be a bulky and lipophilic amino acid such as tryptophan. Again, suitable modified residues are discussed above in relation to the smaller molecules.

Alternatively or in addition an artificial bulky and lipophilic moiety may be provided by an N or C terminal modifying group such as have already been described herein. The peptides may incorporate a bulky and lipophilic moiety at both the N and C terminii, at either the N or C terminus or at neither terminus. Where only one terminus carries a bulky and lipophilic moiety, that will preferably be the C terminus. If the C terminus is not modified by incorporation of a bulky and lipophilic group as defined herein it will preferably be otherwise modified to remove the negative charge normally present at the C terminus at pH 7.0. Suitable C terminal modifications will include amidation or formation of an ester which does not include a bulky and lipophilic moiety, e.g. a short chain alkyl ester such as a methyl ester. Preferably, at least one of the bulky and lipophilic moieties is an artificial bulky and lipophilic moiety.

The artificial bulky and lipophilic moiety will preferably be at least as bulky and lipophilic, if not more bulky and lipophilic, than the bulky and lipophilic R group of any genetically coded amino acid, i.e. at least as bulky and lipophilic as tryptophan. The enhanced bulkiness and lipophillicity resulting in peptides which are highly antimicrobially active. The activity of these peptides would appear to be sequence independent, the presence of particular functional groups (cationic and bulky and lipophilic) are responsible for the molecules' cytotoxic activity.

These peptides are preferably synthesised by standard methods of peptide synthesis from the individual amino acid building blocks. Modified residues may be incorporated during synthesis but the residues may alternatively be modified after synthesis of the full peptide. Non-genetically coded or modified amino acids, aside from any residue incorporating an 'artificial bulky and lipophilic moiety' or an 'artificial cationic moiety', may be incorporated but preferably the peptide will include some or a majority of genetically coded residues. Post synthetic modification may be used to provide an artificial bulky and lipophilic moiety.

Thus, in a further aspect, the present invention provides bioactive peptides of 5 or 6 amino acids in length which incorporate at least 2 bulky and lipophilic moieties and at least 2 cationic moieties, wherein at least one of said bulky and lipophilic moieties is an artificial bulky and lipophilic moiety or at least one of said cationic moieties is an artificial cationic moiety. The use of these peptides as antimicrobial or antitumoural agents and pharmaceutical and other compositions containing them constitute further aspects of the present invention. Of the genetically coded amino acids, arginine, lysine and histidine are cationic residues and tyrosine, phenylalanine, tryptophan, leucine, isoleucine and methionine are bulky and lipophilic residues. 6 residues are preferred and if only 5 amino acids are present, preferably 3 of these are bulky and lipophilic in character.

Peptidomimetic compounds having the structural and functional characteristics of the peptides described above may be prepared and constitute, together with their uses as antimicrobial and antitumoural agents further aspects of the present invention.

These 5 and 6 mer peptides and compositions, particularly pharmaceutical compositions comprising them for use in therapy, e.g. as antitumoural or antimicrobial, particularly antibacterial agents constitute further aspects of the present invention. As discussed previously, there are a range of non-therapeutic uses of active antimicrobial agents and these uses constitute further aspects of the present invention.

In a yet further aspect of the present invention, a class of small peptides incorporating all genetically coded amino acids have been identified with good bioactivity. Thus, the present invention provides bioactive peptides of 5 or 6 amino acids in length which have an unmodified N terminus, all of said amino acids being either cationic or bulky and lipophilic in nature, at least two amino acids being bulky and lipophilic and at least two being cationic.

Peptides in this category are described in Examples 1 and 4. It should be recognised that arginine is used as an example of a genetically coded cationic amino acid and tryptophan or tyrosine as an example of a genetically coded bulky and lipophilic amino acid. The other genetically coded bulky and lipophilic and cationic amino acids have been described previously. Equivalents of the peptides of Examples 1 and 4 incorporating other genetically coded bulky and lipophilic amino acids in place of tryptophan and/or arginine are included within this aspect of the invention. The C terminus of these peptides is unmodified or amidated or esterified with a small non-bulky and lipophilic group. Pharmaceutical compositions comprising these peptides and their use as antimicrobial or antitumoural agents constitute further aspects of the present invention.

The molecules of the invention typically have an antimicrobial e.g. antibacterial, antiviral or antifungal activity. In addition, the molecules exhibit antitumoural activity, the molecules selectively lysing cancer cells rather than healthy eukaryotic cells. The molecules may be lytic, and/or cause a destabilisation of the cell membrane which can effect permeability and cell viability. The molecules are active against Gram negative and Gram positive bacteria but have been shown to be particularly effective against Gram-positive bacteria. Thus the uses, therapies and medicaments are preferably for the treatment of a Gram-positive infection.

The molecules may be bactericidal or bacteriostatic, bactericidal molecules generally being preferred. A high MBC value but a low MIC value is indicative of a bacteriostatic molecule; the dipeptide TbtR OMe for example is bacteriostatic in respect of E. coli. The tripeptide RTbtR OMe which incorporates an additional cationic group is bactericidal. Increasing the cationicity of a molecule is a tool which may be used to provide a bactericidal molecule and thus, in a further aspect, the present invention comprises a method of increasing the bactericidal activity of a peptide as compared to its bacteriostatic activity, said peptide having 2-4 amino acids, at least one more cationic than anionic moiety and at least one super bulky and lipophilic group or at least two bulky and lipophilic groups by increasing by at least one the number of cationic moieties present in the peptide. In general it seems that the presence of at least two, e.g. 3 or 4 additional cationic groups provides active molecules but cationicity can be reduced if the number of bulky and lipophilic groups is increased to compensate.

The invention therefore provides methods of treating microbial infections by administering the various molecules described herein. In particular methods of destabilising microbial cell membranes are provided. The amount administered should be effective to kill all or a proportion of the target microbes or to prevent or reduce their rate of reproduction or otherwise to lessen their harmful effect on the body. The clinician or patient should observe improvement in one or more of the parameters or symptoms associated with the infection. Administration may also be prophylactic.

The peptides of the invention may be synthesised in any convenient way. Generally the reactive groups present (for example amino, thiol and/or carboxyl) will be protected during overall synthesis. The final step in the synthesis will thus be the deprotection of a protected derivative of the invention. As discussed above, certain peptides of the invention will carry a 'protecting group' as this is responsible for enhanced cytotoxicity.

In building up the peptide, one can in principle start either at the C-terminal or the N-terminal although the C-terminal starting procedure is preferred.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzoxy (also designated Z) t-butoxycarbonyl (also designated Boc), 4-methoxy-2,3,6-trimethylbenzene sulphonyl (Mtr) and 9-fluorenylmethoxy-carbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), pentachlorophenyl (OP-ClP), pentafluorophenyl (OPfp) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

Peptides according to the invention may be prepared by incomplete deprotection to leave groups which enhance the cytotoxic activity of the peptides. Alternatively, modified R and N- and C-terminal groups may be prepared after synthesis of the peptide and associated deprotection.

A particularly preferred method involves synthesis using amino acid derivatives of the following formula: Fmoc-amino acid-Opfp.

References and techniques for synthesising peptidomimetic compounds and the other bioactive molecules of the invention are described herein and thus are well known in the art.

Formulations comprising one or more small bioactive molecules as defined herein in admixture with a sutiable diluent, carrier or excipient constitute a further aspect of the present invention. Such formulations may be for, inter alia, pharmaceutical (including veterinary) or agricultural purposes or for use as sterilising agents for materials susceptible to microbial contamination, e.g. in the food industry. Suitable diluents, excipients and carriers are known to the skilled man.

The peptides and other molecules defined herein exhibit broad antimicrobial activity and thus are also suitable as antiviral and antifungal agents, which will have pharmaceutical and agricultural applications, and as promoters of wound healing or spermicides. All of these uses constitute further aspects of the invention.

Methods of treating or preventing bacterial, viral or fungal infections or of treating tumours which comprises administration to a human or animal patient one or more of the peptides, peptidomimetics or other bioactive molecules as defined herein constitute further aspects of the present invention.

The compositions according to the invention may be presented, for example, in a form suitable for oral, nasal, parenteral, intravenal, intratumoral or rectal administration.

As used herein, the term "pharmaceutical" includes veterinary applications of the invention.

The active compounds defined herein may be presented in the conventional pharmacological forms of administration, such as tablets, coated tablets, nasal sprays, solutions, emulsions, liposomes, powders, capsules or sustained release forms. The peptides are particularly suitable for topical administration, e.g. in the treatment of diabetic ulcers. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays which are a preferred method of administration may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the active molecules preferably contain 0.1-10 mg, for example 1-5 mg of the antimicrobial agent. The pharmaceutical compositions may additionally comprise further active ingredients, including other cytotoxic agents such as other antimicrobial peptides. Other active ingredients may include different types of antibiotics, cytokines e.g. IFN-γ, TNF, CSF and growth factors, immunomodulators, chemotherapeutics e.g. cisplatin or antibodies.

The bioactive molecules, when used in topical compositions, are generally present in an amount of at least 0.1%, by weight. In most cases, it is not necessary to employ the peptide in an amount greater than 1.0%, by weight.

In employing such compositions systemically (intramuscular, intravenous, intraperitoneal), the active molecule is present in an amount to achieve a serum level of the bioactive molecule of at least about 5 ug/ml. In general, the serum level need not exceed 500 ug/ml. A preferred serum level is about 100 ug/ml. Such serum levels may be achieved by incorporating the bioactive molecule in a composition to be administered systemically at a dose of from 1 to about 10 mg/kg. In general, the molecule(s) need not be administered at a dose exceeding 100 mg/kg.

Methods of treating environmental or agricultural sites or products, as well as foodstuffs and sites of food production with one or more of the bioactive molecules as defined herein to reduce the numbers of viable bacteria present or limit bacterial growth or reproduction constitute further aspects of the present invention.

BRIEF DESCRIPTION OF THE DRAWINGS

The invention will now be further described with reference to the following non-limiting Examples and the figures in which.

EXAMPLES

Figure 1:
FIG. 1 is an electronmicrograph of normal (untreated) *E. coli*.
Figure 2:
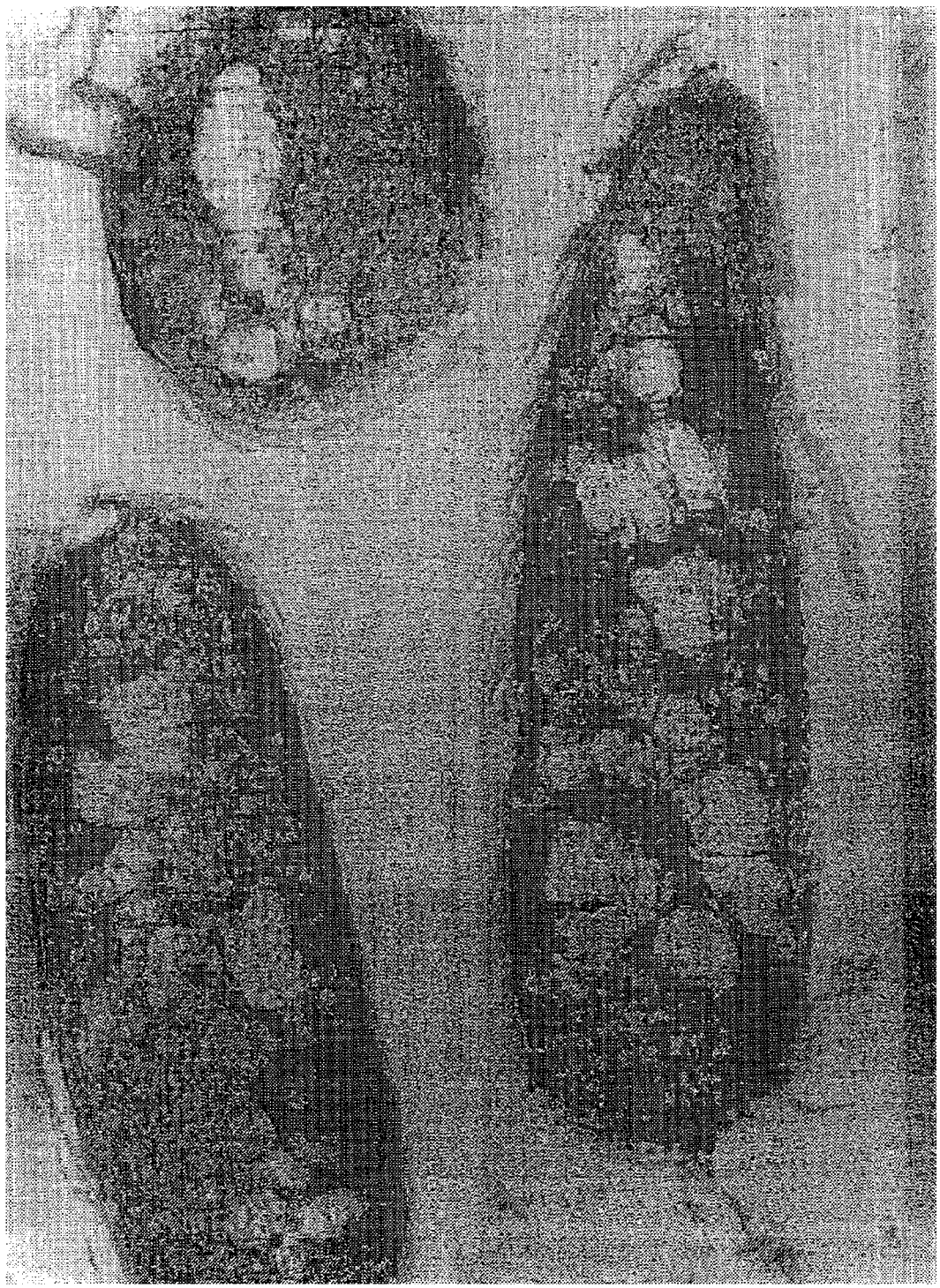
FIG. 2 is an electronmicrograph of *E. coli* treated with one of the peptides described herein, WRWRWR. [SEQ ID NO: 1]. The treated bacteria are void of cytoplasmic matter and their cell membranes (as well as cell wall components) are destroyed, clearly indicating a lytic mechanism.

The following experiments exemplify the principles discussed above. For convenience, cationic amino acids are represented by arginine and bulky and lipophilic amino acids by tryptophan, tyrosine and tri-tert.-butyl tryptophan (super bulky and lipophilic). It is clear that other residues with similar charge or bulk and lipophilicity could be used in place of these amino acids. N and C terminal modifying groups provide further bulky and lipophilic groups.

The antimicrobial efficacy was determined as the minimum inhibitory concentration (MIC) and minimum bactericidal concentration (MBC) both in µg/ml for *E. coli* and *S. aureus*, representative Gram-negative and Gram positive bacteria. The cellular toxicity was determined as EC50 (amount of peptide necessary for 50% lysis of erythrocytes).

MIC (Minimum Inhibitory Concentration) Tests

The bacterial strains used were: *Escherichia coli* ATCC 25922, *Staphylococcus aureus* ATCC 25923, MRSA ATCC 33591 and MRSE ATCC 27626. All strains were stored at −70° C. The bacteria were grown in 2% Bacto Peptone water (Difco 1807-17-4). All tests were performed with bacteria in mid-logarithmic growth phase. Determination of the minimum inhibitory concentration (MIC) of the peptides for bacterial strains were performed in 1% Bacto Peptone water. A standard microdilution technique with an inoculum of $2 \times 10^6$ CFU/ml was used. All assays were performed in duplicate. Since the peptides are positively charged and therefore could adhere to the plastic wells, we controlled the actual concentration of the peptides in the solution by HPLC. There was no difference between the concentration of the peptides before or after adding the solution to the plastic wells. MBC tests were performed in an analogous manner.

Hemolytic Assay

The hemolytic activities of the peptides were determined using fresh human red blood cells. 8 ml blood was taken from a healthy person. 4 ml blood was transferred to a polycarbonate tube containing heparin to a final concentration of 10 U/ml, and the remaining 4 ml blood was transferred to a glass tube containing EDTA with final concentration of 15% EDTA. The erythrocytes were isolated from heparin-treated blood by centrifugation in 1500 rpm for 10 min and washed three times with phosphate-buffered saline (PBS) to remove plasma and buffy coat. The cell pellet was resuspended in PBS to make the final volume of 4 ml. The peptide was diluted to a concentration of 2 mg/ml and 0.1 mg/ml. The peptide was further diluted to the concentrations as stated in Table 15. For each tube PBS was added first, then RBCs and peptide solutions. The hematocrit in the blood treated with EDTA was determined after 30 min with Sysmex K-1000, and the resuspended RBCs were diluted into 10% hematocrit. RBCs in PBS (1%) with and without peptides (Table 15) were incubated in a shaker at 37° for 1 hour and then centrifuged at 4000 rpm for 5 min.

The supernatant were carefully transferred to new polycarbonate tubes and the absorbance of the supernatant was measured at 540 nm. Baseline hemolysis was hemoglobin released in the presence of PBS, and 100% hemolysis was hemoglobin released in the presence of 0.1% Triton X-100.

Example 1

A series of peptides was prepared on a solid phase multiple peptide synthesizer MBS 396 from Advance Chemtech with Arg-Trp combinations with C-terminal amidation to avoid negative charge from the carboxylate. The antibacterial activity of these peptides is shown in Table 1 below.

TABLE 1

Antibacterial activity of short RW and similar peptide amides

| Sequence | MIC E. coli | MBC E. coli | MIC S. aureus | MBC S. aureus |
|---|---|---|---|---|
| WRWRWR [SEQ ID NO:1]; | 7.5 | 15 | 7.5 | 10 |
| RRRWWW [SEQ ID NO:2]; | 10 (20) | 20 | 5 (<2.5) | 10 (20) |
| RWWWRR [SEQ ID NO:3]; | 10 | 15 | 7.5 | 10 |
| WWRRRW [SEQ ID NO:4]; | 20 (20) | 20 | 10 (<2.5) | 20 (25) |
| RWRWRW [SEQ ID NO:5]; | 10 (20) | 20 | 5 (<2.5) | 10 |
| RWRYRW [SEQ ID NO:6]; | 50 (10) | | 10 (<2.5) | |
| WRWRW [SEQ ID NO:7]; | 20 (10) | 50 | 5 (<2.5) | 20 (20) |
| WRYRW [SEQ ID NO:8]; | 75 (20) | | 50 (<2.5) | |
| RWRWR [SEQ ID NO:9]; | 50 (20) | 100 | 20 | 20 |
| WRWRY [SEQ ID NO:10]; | 75 (20) | | 50 (<2.5) | |
| RWWR [SEQ ID NO:11]; | >100 | >100 | 10 | >100 |
| WRRW [SEQ ID NO:12]; | >100 | >100 | 75–100 | >100 |
| WRWR [SEQ ID NO:13]; | >100 | >100 | 100 | >100 |
| WRW [SEQ ID NO:14]; | >100 | >100 | 75 | 100 |
| RWR [SEQ ID NO:15] | >100 | >100 | >100 | >100 |

The values in brackets refer to peptides in which one or more of the tryptophan residues have been modified by the PMC group.

Example 2

A second series of peptides was prepared manually by synthesis in solution incorporating an Arg/Trp (Tbt) or Trp (Tbt)/Arg motif with C-terminal esterification and/or N-terminal acylation. The second set of peptides were designed on the basis of preparing a small number of building blocks (i.e. Boc RW OBz, Boc WE OMe and Boc TbtR OMe) and modifying these with additional amino acids (at the N-terminus), N-terminal acylation and/or Cterminal modification (preparation of a cationic site at C-terminus by making a diamino ethane derivative).

General Procedure for the Removal of Boc

The Boc protected peptide was dissolved in reagent K$^i$ and stirred at room temperature for 60-90 minutes.[1] To the reaction mixture was added a solution of p-toluensulphonic acid (2.0-2.5 eq) dissolved in a minimal amount of diethylether[1] and the milky white mixture was cooled in the refrigerator overnight to allow the product to completely precipitate. The ether layer was drained off, and the residue triturated with diethylether before evaporation in vacuo to a powder. The crude product was purified by RP-HPLC prior to biological testing, or used in the next step without further purification.

Boc-D-Arg-D-Trp-OBzl (KP-2-1)

To a stirred solution of Boc-D-Arg-OH hydrochloride (855 mg, 2.75 mmoles), H-D-Trp-OBzl hydrochloride (832 mg, 2.5 mmoles), HOBt (1378 mg, 9 mmoles) and DIPEA (2.05 ml, 12 mmoles) in DMF (5 ml) and dichloromethane (1 ml) cooled on ice was added HBTU (1138 mg, 3 mmoles) in small portions over 10 minutes. The mixture was stirred on ice for 1 hour, 40 ml dichloromethane was added and the organic phase washed successivly with 3×40 ml saturated NaHCO$_3$, 2×30 ml 5% citric acid, 50 ml water and 2×30 ml brine. Evaporation afforded a white solid.

H-D-Arg-D-Trp-OBzl (KP-2-2-1)

Boc-D-Arg-D-Trp-OBzl (1.29 g, 2.2 mmoles) was treated with reagent K as described in the general procedure. Evaporation after removal of the etheral layer afforded 0.85 g of a yellowish solid.

Boc-L-Ara-L-Trp-OBzl (KP-1-2)

To a stirred solution of Boc-L-Arg-OH (792 mg, 2.75 mmoles), H-L-Trp-OBzl hydrochloride (832 mg, 2.5 mmoles), HOBt (1378 mg, 9 mmoles) and DIPEA (2.05 ml, 12 mmoles) in DMF (6 ml) and dichloromethane (3 ml) cooled on ice was added HBTU (1138 mg, 3 mmoles) in small portions over 10 minutes. The mixture was stirred on ice for 45 minutes and at room temperature for 45 minutes. Workup was performed as described for KP-2-1. Evaporation afforded 1.7 g of a yellowish solid.

H-L-Arg-L-Trp-OBzl (KP-4-1)

Boc-L-Arg-L-Trp-OBzl (1.0 g, 1.5 mmoles) was treated with reagent K as described in the general procedure. Evaporation after removal of the etheral layer afforded 1.07 g of a beige solid.

Boc-L-Trp-L-Ara-OMe (KP-3-2)

To a stirred solution of Boc-L-Trp-OH (761 mg, 2.5 mmoles), H-L-Arg-OMe dihydrochloride (718 mg, 2.75 mmoles), HOBt (1378 mg, 9 mmoles) and DIPEA (2.05 ml, 12 mmoles) in DMF (5 ml) and dichloromethane (2 ml) cooled on ice was added HBTU (1138 mg, 3 mmoles) in small portions over 10 minutes. The mixture was stirred on ice for 1 hour, 40 ml ethyl acetate was added and the organic phase washed successivly with 3×40 ml saturated NaHCO$_3$, 2×30 ml 5% citric acid, 50 ml water and 2×30 ml brine. Evaporation afforded 1.1 g of a white solid.

H-L-Trp-L-Arg-OMe (KP-5-1)

Boc-L-Trp-L-Arg-OMe (1.1 g, 2.15 mmoles) was treated with reagent K as described in the general procedure. Evaporation after removal of the etheral layer afforded 1.23 g of a yellowish solid.

Boc-L-Trp-L-Trp-L-Arg-OMe (KP-6-1)

To a stirred solution of Boc-L-Trp-OH (87 mg, 0.29 mmoles), H-L-Trp-L-Arg-OMe di-p-toluenesulphonic acid (226 mg, 0.3 mmoles), HOBt (158 mg, 1.03 mmoles) and DIPEA (235 μl, 1.37 mmoles) in DMF (2 ml) cooled on ice was added HBTU (130 mg, 0.34 mmoles) in small portions over 10 minutes. The mixture was stirred on ice for 80 minutes, 5 ml dichloromethane was added and the organic phase washed successivly with 3×5 ml saturated NaHCO$_3$, 2×5 ml 5% citric acid, 5 ml water and 5 ml brine. Evaporation afforded 0.05 g of a yellow oil which, as judged by Tlc, contained only minor amounts of product. The pooled water phases were extracted with 3×15 ml ethyl acetate, dried over MgSO$_4$ and evaporated to afford 0.17 g of an yellow oil. This oil was used in the next step without further purufication.

H-L-Trp-L-Trp-L-Arg-OMe (KP-8-1)

Boc-L-Trp-L-Trp-L-Arg-OMe (0.14 g, ca 0.2 mmoles) was treated with reagent K as described in the general procedure. The product was precipitated by the addition of diethyl ether without added p-toluenesulphonic acid.

Boc-L-Arg-L-Trp-L-Arg-OMe (KP-11-1)

To a stirred solution of Boc-L-Arg-OH (64 mg, 0.22 mmoles), H-L-Trp-L-Arg-OMe di-p-toluenesulphonic acid (175 mg, 0.23 mmoles), HOBt (128 mg, 0.83 mmoles) and DIPEA (181 µl, 1.1 mmoles) in DMF (1 ml) cooled on ice was added HBTU (106 mg, 0.28 mmoles) in small portions over 10 minutes. The mixture was stirred on ice for 2 hours and at room temperature for 30 minutes, 10 ml ethyl acetate was added and the organic phase washed as described for KP-3-2. After workup, the organic layer contained no amount of the desired product as judged by analytical RP-HPLC. The pooled water phases were extracted with 3×15 ml ethyl acetete and evaporated to afford 0.1 g of an yellow oil. This oil was used in the next step without further purification.

H-L-Arg-L-Trp-L-Arg-OMe (KP-13-1)

Boc-L-Trp-L-Trp-L-Arg-OMe (0.14 g, ca 0.2 mmoles) was treated with reagent K as described in the general procedure. The pruduct was precipitated by the addition of diethyl ether without added p-toluenesulphonic acid. Evaporation after removal of the etheral layer afforded 0.1 g of a white solid.

Boc-L-Trp-L-Arg-L-Trp-OBzl (KP-12-1)

To a stirred solution of Boc-L-Trp-OH (88 mg, 0.29 mmoles), H-L-Arg-L-Trp-OBzl di-p-toluenesulphonic acid (255 mg, 0.3 mmoles), HOBt (158 mg, 1.03 mmoles) and DIPEA (235 µl, 1.37 mmoles) in DMF (2 ml) cooled on ice was added HBTU (130 mg, 0.34 mmoles) in small portions over 10 minutes. The mixture was stirred on ice for 2 hours and at room temperature for 30 minutes, 10 ml ethyl acetate was added and the organic phase washed as described for KP-3-2. Evaporation afforded 0.23 g of a yellow oil.

H-L-Trp-L-Arg-L-Trp-OBzl (KP-14-1)

Boc-L-Trp-L-Arg-L-Trp-OBzl (0.23 g, ca 0.3 mmoles) was treated with reagent K as described for KP-8-1. Evaporation after removal of the etheral layer afforded 0.2 g of a white solid.

Boc-D-Trp-L-Arg-L-Trp-OBzl (KP-15-1)

To a stirred solution of Boc-D-Trp-OH (90 mg, 0.29 mmoles), H-L-Arg-L-Trp-OBzl di-p-toluenesulphonic acid (251 mg, 0.3 mmoles), HOBt (158 mg, 1.03 mmoles) and DIPEA (235 µl, 1.37 mmoles) in DMF (5 ml) cooled on ice was added HBTU (130 mg, 0.34 mmoles) in small portions over 10 minutes. The mixture was stirred on ice for 40 minutes, and workup performed as described for KP-2-1. Evaporation afforded 0.24 g of a white solid.

H-D-Trp-L-Arg-L-Trp-OBzl (KP-16-1)

Boc-Trp-Arg-Trp-OBzl (0.24 g, ca 0.3 mmoles) was treated with reagent K as described in the general procedure. Evaporation after removal of the etheral layer afforded 0.17 g of a beige solid.

Boc-D-Trp-D-Arg-D-Trp-OBzl (KP-2-1-2)

To a stirred solution of Boc-D-Trp-OH (162 mg, 0.53 mmoles), H-D-Arg-D-Trp-OBzl di-p-toluenesulphonic acid (464 mg, 0.56 mmoles), HOBt (292 mg, 1.9 mmoles) and DIPEA (4.4 ml, 25 mmoles) in DMF (5 ml) and dichloromethane (1 ml) cooled on ice was added HBTU (241 mg, 0.64 mmoles) in small portions over 10 minutes. The mixture was stirred on ice for 70 minutes, 10 ml dichloromethane was added and the organic phase washed successivly with 3×10 ml saturated NaHCO$_3$, 4×10 ml 5% citric acid (until acidic water phase due to too much DIPEA added), 2×10 ml water and 2×10 ml brine. Evaporation afforded 0.42 g crude product.

H-D-Trp-D-Arg-D-Trp-OBzl (KP-2-1-3)

Boc-D-Trp-D-Arg-D-Trp-OBzl (0.38 g, ca 0.4 mmoles) was treated with reagent K as described in the general procedure. Evaporation after removal of the etheral layer afforded 0.3 g of a beige solid.

Boc-L-Arg-L-Trp-OH (KP-10-2)

To a solution of Boc-L-Arg-L-Trp-OH (300 mg, 0.5 mmoles) in 5 ml methanol/water (19:1) Pd-10% on charcoal (53 mg, 0.05 mmoles) was added. The mixture was stirred under a hydrogen atmosphere (1 atm) overnight, filtered through a thin layer of Celite 545 and evaporated to afford a red oil. The oil was dissolved in water under gentle heating and lyophilized to afford 383 mg of a pink powder.

Boc-L-Arg-L-Trp-L-Ara-L-Trp-OBzl (KP-17-1) [SEQ ID NO:16 ]

To a stirred solution of Boc-L-Arg-L-Trp-OH hydrochloride (100 mg, 0.20 mmoles), H-L-Arg-L-Trp-OBzl di-p-toluenesulphonic acid (175 mg, 0.21 mmoles), HOBt (110 mg, 0.72 mmoles) and DIPEA (164 µl, 0.96 mmoles) in DMF (2 ml) cooled on ice was added HBTU (91 mg, 0.24 mmoles) in small portions over 10 minutes. The mixture was stirred on ice for 3 hours and workup performed as described for KP-3-2.

H-L-Arg-L-Trp-L-Arg-L-Trp-OBzl (KP-19-1) [SEQ ID NO:17 ]

Boc-L-Arg-L-Trp-L-Arg-L-Trp-OBzl (ca 0.2 mmoles) was treated with reagent K as described for KP-8-1. Complete removal of the etheral layer was difficult to perform without loss of material and the pink crude product therefore probably contained significant amounts of TFA.

Boc-L-Ara-L-Trp-D-Arg-D-Trp-OBzl (KP-18-1) [SEQ ID NO:18 ]

To a stirred solution of Boc-L-Arg-L-Trp-OH hydrochloride (100 mg, 0.20 mmoles), H-D-Arg-D-Trp-OBzl di-p-toluenesulphonic acid (175 mg, 0.21 mmoles), HOBt (110 mg, 0.72 mmoles) and DIPEA (164 µl, 0.96 mmoles) in DMF (2 ml) cooled on ice was added HBTU (91 mg, 0.24 mmoles) in small portions over 10 minutes. The mixture was stirred on ice for 3 hours and workup performed as described for KP-3-2. After workup, the organic layer contained only minor amounts of the desired product as judged by analytical RP-HPLC. The pooled water phases was extracted with 3×15 ml ethyl acetete and evaporated to afford the crude product.

H-L-Arg-L-Trp-D-Arg-D-Trp-OBzl (KP-20-1) [SEQ ID NO:19 ]

Boc-L-Arg-L-Trp-D-Arg-D-Trp-OBzl (ca 0.2 mmoles) was treated with reagent K as described for KP-8-1. Complete removal of the etheral layer was difficult to perform without loss of material and the crude product therefore probably contained significant amounts of TFA.

Boc-L-Arg-L-Trp-L-Trp-L-Arg-OMe (KP-21-1) [SEQ ID NO:20]

To a stirred solution of Boc-L-Arg-L-Trp-OH hydrochloride (100 mg, 0.20 mmoles), H-L-Trp-L-Arg-OMe di-p-toluenesulphonic acid (171 mg, 0.23 mmoles), HOBt (110 mg, 0.72 mmoles) and DIPEA (164 µl, 0.96 mmoles) in DMF (2 ml) cooled on ice was added HBTU (91 mg, 0.24 mmoles) in small portions over 10 minutes. The mixture was stirred on ice for 3 hours and workup performed as described for KP-3-2. After workup, the organic layer contained only minor amounts of the desired product as judged by analytical RP-HPLC. The pooled water phases were extracted with 3×15 ml ethyl acetate and evaporated to afford 0.16 g of a yellow oil.

H-L-Arg-L-Trp-L-Trp-L-Arg-OMe (KP-22-1) [SEQ ID NO:21]

Boc-L-Arg-L-Trp-L-Trp-L-Arg-OMe (0.16 g, ca 0.18 mmoles) was treated with reagent K as described for KP-8-1. Evaporation after removal of the etheral layer afforded 0.12 g of a pink solid.

Ind-Trp-Arg-OMe

3-Indolylacetic acid (0.289 mmoles) was treated with H-Trp-Arg-OMe (1.06 eq), triethylamine (2.01 eq) and HBTU (1.10 eq) as described for Boc-Trp-Arg-OMe. Methanol was used as solvent. The reaction was quenched by adding 9 ml saturated sodium chloride. The aquous phase was extracted 3×7 ml ethyl acetate and the organic phase washed with 4 ml 2 M hydrochlorid acid, 4 ml water and 4 ml 5% sodium hydrogen carbonate. The washing procedure was repeated one time before the organic phase was dried with 5 ml saturated sodium chloride and then evaporated to yield 0.11 g of a white solid. The crude product was purified by RP-HPLC.

$^1$H NMR (acetonitril-$d_3$): δ=1.34 (2H, m), 1.52 (1H, m), 1.71 (1H, m), 2.89 (5H, m), 3.05 (1H, m), 3.15 (1H, m), 4.34 (1H, m), 4.48 (1H, m), 6.01 (4H, bs), 6.42 (1H, bs), 6.88-7.50 (12H, ms), 9.10 (1H, s), 9.22 (1H, s).

Chx-Trp-Arg-OMe

Cyclohexane carboxylic acid (0.297 mmoles) was treated with H-Trp-Arg-OMe (1.03 eq), triethylamine (1.96 eq) and HBTU (1.05 eq) as described for Boc-Trp-Arg-OMe. Methanol was used as solvent. Quenching and work up was performed as for Ind-Trp-Arg-OMe to yield 0.10 g of a white solid. The crude product was purified by RP-HPLC.

Boc-Tbt-Arg-OMe

A stirred solution of Boc-Tbt-OH (0.4735 g, 1.0 mmole), H-Arg-OMe dihydrochloride (0.2741 g, 1.05 mmoles), HOBt (0.4872 g, 3.61 mmoles) and DIPEA (0.820 ml, 4.79 mmoles) in DMF/dichloromethane (14 ml) is cooled in an ice/water bath. HBTU (0.4560 g, 1.2 mmoles) is added in small portions over 10 min. The mixture is stirred for 30 min and the cooling bath removed. The reaction mixture is allowed to stir at room temperature until no carboxylic acid component is left (Tlc system A). The mixture is evaporated to an oil, 20 ml dichloromethane is added and the organic phase washed 3×20 ml saturated sodium hydrogen carbonate, 2×15 ml 5% citric acid, 25 ml water and 2×15 ml saturated sodium chloride successively, and evaporated to give 0.80 g of a white solid.

H-Tbt-Arg-OMe

Boc-Tbt-Arg-OMe (0.90 mmoles) was treated with reagent K as described in the general method. Evaporation after removal of the etheral layer afforded 0.24 g of a white solid. The crude product was purified by RP-HPLC.

Boc-Arg-Tbt-Arg-OMe

The di-p-toluensulfonic acid salt of H-Tbt-Arg-OMe (0.24 g, 0.270 mmoles), Boc-Arg-OH (0.0933 g, 0.335 mmoles), HOBt (0.0442 g, 0.327 mmoles), triethylamine (0.113 ml, 0.811 mmoles) and HBTU (0.1231 g, 0.325 mmoles) were dissolved in acetonitrile (2.2 ml, HPLC-grade) and stirred at room temperature. After 1 hr starting material was still left (Tlc system A). Three equivalents of triethylamine were added and the reaction mixture stirred for another hr. Quenching and workup was performed as described for Boc-Trp-Arg-OMe. The crude oil was coevaporated with dichloromethane to afford 0.23 g of a white powder. The crude product was used without further purifications.

H-Arg-Tbt-Arg-OMe

The crude Boc-Arg-Tbt-Arg-OMe was dissolved in 4.05 ml of reagent K and the cleavage performed as described in the general procedure. The crude product was purified by RP-HPLC prior to biological testing.

Boc-Arg-Trp-OBzl

Boc-Arg-OH and H-Trp-OBzl coupled as described for Boc-Trp-Arg-OMe. N-methyl morpholine used as base. The crude product was purified by RP-HPLC.

H-Arg-Trp-OBzl

The crude Boc-Arg-Trp-OBzl (1.23 mmoles) was dissolved in 18.3 ml of reagent K and the cleavage performed as described in the general procedure. The crude product was used without further purification.

Ind-Ara-Trp-OBzl

3-Indolylacetic acid (0.0450 g, 0.257 mmoles) was treated with H-Arg-Trp-OBzl di-p-toluensulphonic acid salt, HBTU and triethylamine (6 eq) as described for Boc-Trp-Arg-OMe. Acetonitrile was used as solvent. The crude product was isolated as 0.19 g of a white solid.

Chx-Ara-Trp-OBzl

Cyclohexane carboxylic acid (0.0031 ml, 0.266 mmoles) was treated with H-Arg-Trp-OBzl di-p-toluensulphonic acid salt, HBTU and triethylamine (6 eq) as described for Boc-Trp-Arg-OMe. Acetonitrile was used as solvent. The crude product was isolated as 0.17 g of a white solid.

Ind-Arg-Trp-OH

The crude Ind-Arg-Trp-OBzl was hydrogenated as described in the general method to afford an yellow oil.

Chx-Arg-Trp-OH

The crude Chx-Arg-Trp-OBzl was hydrogenated as described in the general method to afford an yellow oil.

Boc-Arg-Trp-OH (B87)

The crude Boc-Arg-Trp-OBzl was hydrogenated as described in the general method to afford 0.72 g of an yellow oil.

Boc-Arg-Trp-Dae-Z

To a stirred solution of Boc-Arg-Trp-OH (1.265 mmoles) in DMF/dichloromethane (12 ml, 1:1), HOBt (0.6202 g, 4.590 mmoles), DIPEA (1.040 ml, 6.075 mmoles) and N-Z-diaminoethane hydrochloride (0.3088 g, 1.339 mmoles) were added. HBTU (0.5772 g, 1.522 mmoles) was added in small portions over 5 min. The reaction mixture was stirred at room temperature for 3 hrs and 45 min and evaporated to a dark yellow oil. The oil was dissolved in 20 ml ethylacetate and washed with 3 ml 2 M hydrochloric acid, 5 ml water 5 ml 5% sodium hydrogen carbonate and 5 ml water successively. The resulting dark yellow solution was dried over magnesium sulphate and evaporated to an oil. Trituration in heptane failed, and the oil was evaporated to yield 0.86 g of a brownish solid.

H-Arg-Trp-Dae-Z

Boc-Arg-Trp-Dae-Z (0.544 mmoles) was dissolved in reagent K (6.8 ml TFA) and stirred at room temperature for 1 hr and 10 minutes. The reaction mixture was evaporated to a small volume and a solution of p-toluensulphonic acid (0.32 g) in diethylether (20 ml) was added. The milky white mixture was cooled in the refrigerator overnight to allow the product to completely precipitate. The ether layer was drained off, and the residue evaporated in vacuo to afford a white powder. The crude product was purified by RP-HPLC.

Ind-Ara-Trp-Dae-Z

3-Indolylacetic acid (0.0265 g, 0.153 mmoles) was treated with H-Arg-Trp-Dae-Z di-p-toluensulphonic acid salt, HBTU (1.2 eq) and triethylamine (5 eq) as described for Boc-Trp-Arg-OMe. Acetonitrile (1.4 ml) and DMF (0.6 ml) were used as solvents, due to poor solubility of the dipeptide analog in acetonitrile. The crude product was isolated as 0.12 g of a white solid.

ABBREVIATIONS

| Arg | arginine |
|---|---|
| Boc | t-butyloxycarbonyl |
| Chx | cyclohexane carboxylic acid |
| Dae | diamino ethane |
| DIPEA | diisopropylethylamine |
| DMF | N,N'-dimethylformamide |
| ESMS | Electrospray Mass Spectrometry |
| HBTU | O-(Benzotriazol-1-yl)N,N,N',N'-tetramethyluronium hexafluorophosphate |
| HOBt | 1-hydroxybenzotriazole |
| Ind | 3-indolylacetic acid |
| MBC | Minimum Bactericidal Concentration |
| MIC | Minimum Inhibitory Concentration |
| RP-HPLC | Reversed Phase High Performance Liquid Chromatography |
| Tbt | 2,5,7-tri-t-butyl tryptophan |
| TFA | Trifluoroacetic acid |
| Trp | tryptophan |
| Z | benzyloxycarbonyl |

REFERENCES

1) Guy, C. A.; Fields, G. B. *Methods in enzymology* 1997, 289, 67-83.
2) Lott, R. S.; Chauhan, V. S.; Stammer, C. H. *Journal of the Chemical Society Chemical Conmmunications* 1979, 495-496.

Notes i Reagent K consists of phenol (5%, w/v), water (5% v/v), thioanisole (5% v/v), ethanedithiol (2.% v/v) and trifluoroacetic acid (82.5% v/v). 1.5 ml of the reagent per mmoles of the peptide is used for cleavage of the Boc group.

ii The addition of p-toluenesulphonic acid in diethyl ether results in the formation of the p-toluenesulphonic acid salts of the peptides. Peptides containing one free amino function or a guanidine function are believed to form the mono p-toluenesulphonic acid salt etc.

Identification of the products was performed using ESMS and the results are shown in Table 2.

TABLE 2

Analytical results for peptides

| Sequence[a] | Code | MW | ESMS | Purity |
|---|---|---|---|---|
| RW-OBzl [SEQ ID NO:22]; | KP-4-1/1 | 450.53 | 451.1 | 97% |
| rw-OBzl [SEQ ID NO:23]; | KP-2-2-1 | 450.53 | 451.1 | 98% |
| WR-OMe [SEQ ID NO:24]; | KP-5-1/1 | 374.44 | 375.2 | 97% |
| WRW-OBzl [SEQ ID NO:25]; | KP-14-1/1 | 636.73 | 637.4 | 98% |
| wrw-OBzl [SEQ ID NO:26]; | KP-2-1-3 | 636.73 | 637.3 | 97% |
| wRW-OBzl [SEQ ID NO:27]; | KP-16-1/1 | 636.73 | 637.4 | 98% |
| WWR-OMe [SEQ ID NO:28]; | KP-8-1/1A | 560.64 | 561.4 | 97% |
| RWR-OMe [SEQ ID NO:29]; | KP-13-1/1 | 560.64 | 531.4 | 98% |
| RWRW-OBzl [SEQ ID NO:30]; | KP-19-l/2u | 792.93 | 793.4 | 97% |
| RWrw-OBzl [SEQ ID NO:31]; | KP-20-1/1 | 792.93 | 793.4 | 98% |
| RWWR-OMe [SEQ ID NO:32] | KP-22-1 | 716.84 | 717.4 | 99% |

[a]Capital letters represent L-amino acids, non-capital letters represent D-amino acids The chemical yield of the coupling and deprotection reactions has not been measured. Identification of the products has been done using ESMS. Purification has been performed with RP-HPLC on a semi-preparative C18 coloumn with water and acetonitrile (both added 0.01% TFA) as mobile phase. Peptide content in the purified samples has been establised with RP-HPLC on an analytical C18 coloumn.

The antibacterial activity of these peptides is shown in Tables 3-5 below.

TABLE 3A

Antibacterial activity of short peptide derivatives[a] Sequence[b]

| Sequence[b] | MIC E. coli | | MIC S. aureus | | MIC MRSA | | MIC MRSE | |
|---|---|---|---|---|---|---|---|---|
| RW-OBzl [SEQ ID NO:22] | >200 | >200 | 50 | 50 | 25/50 | 20 | 20 | 20 |
| rw-OBzl [SEQ ID NO:23] | >200 | >200 | 50 | 50 | 50/75 | 50 | 20 | 20 |
| WR-OMe [SEQ ID NO:24] | >200 | >200 | >200 | =200 | >200 | >200 | >200 | >200 |

TABLE 3A-continued

Antibacterial activity of short peptide derivatives[a] Sequence[b]

| Sequence[b] | MIC E. coli | | MIC S. aureus | | MIC MRSA | | MIC MRSE | |
|---|---|---|---|---|---|---|---|---|
| WRW-OBzl [SEQ ID NO:25] | 75 | 75 | 5 | 5 | 5 | 2.5 | 5 | 5 |
| wrw-OBzl [SEQ ID NO:26] | 100 | 50 | 5 | 5 | 5 | 5 | 5 | 5 |
| wRW-OBzl [SEQ ID NO:27] | 75 | 75/100 | 20 | 20 | 20 | 10 | 10 | 10 |
| WWR-OMe [SEQ ID NO:28] | >200 | >200 | >200 | =200 | 200 | 200 | 200 | 200 |
| RWR-OMe [SEQ ID NO:29] | >200 | >200 | >200 | >200 | 200 | >200 | 100 | 100 |
| RWRW-OBzl [SEQ ID NO:30] | 75/100 | 75 | 5 | 5 | 5 | 5 | 2.5 | 2.5 |
| RWrw-OBzl [SEQ ID NO:31] | 75 | 50/75 | 5 | 5 | 5 | 2.5 | 2.5 | — |
| RWWR-OMe [SEQ ID NO:32] | >200 | >200 | 75 | 75 | 50 | 50 | 20 | 20 |

[a]Concentration series: 200, 100, 75, 50, 25, 10, 5 and 2.5 µg/ml.
[b]Capital letters represent L-amino acids, non-capital letters represent D-amino acids

TABLE 3B

| | MIC values in µg/ml | | | |
|---|---|---|---|---|
| | E. coli | S. aureus | MRSA | MRSE |
| Rw-OBzl | >300 | 37.5 | 37.5 | 25 |
| rW-OBzl | >300 | 37.5 | 50 | 25 |
| WR-OBzl | >300 | 100 | 37.5 | |
| KW-OBzl | >300 | 37.5 | 37.5 | 25 |
| kW-OBzl | >300 | 100 | | |
| RF-OBzl | >300 | 300 | 150 | 100 |
| FR-OBzl | >300 | >300 | 37.5 | 100 |
| KF-OBzl | >300 | 300 | 300 | 150 |

Concentration series: 300, 100, 50, 37.5 and 25 µg/ml Capital Letters represent L-amino acids, non-capital letters represent D-amino acids

TABLE 4

Antibacterial activity of short peptide derivatives[a]

| Sequence[b] | MBC E. coli | | MBC S. aureus | | MBC MRSA | | MBC MRSE | |
|---|---|---|---|---|---|---|---|---|
| RW-OBzl [SEQ ID NO:22] | >200 | >200 | 50 | 50 | 75 | 50 | 20 | 20 |
| rw-OBzl [SEQ ID NO:23] | >200 | >200 | 75 | 100 | 100 | 75 | 25/50 | 25 |
| WR-OMe [SEQ ID NO:24] | >200 | >200 | >200 | >200 | >200 | >200 | >200 | >200 |
| WRW-OBzl [SEQ ID NO:25] | 200 | 200 | 5 | 5 | 10 | 10/20 | 10 | 5 |
| wrw-OBzl [SEQ ID NO:26] | 200 | 200 | 5 | 10 | 10 | 10 | 5 | 5 |
| wRW-OBzl [SEQ ID NO:27] | 200 | 100 | 20 | 20 | 20 | 10 | 10 | 10 |
| WWR-OMe [SEQ ID NO:28] | >200 | >200 | >200 | >200 | 200 | 200 | 200 | 200 |
| RWR-OMe [SEQ ID NO:29] | >200 | >200 | >200 | >200 | >200 | >200 | 200 | 200 |
| RWRW-OBzl [SEQ ID NO:30] | 100 | 100 | 10 | 5 | 10 | 5 | 2.5/5 | 2.5 |
| RWrw-OBzl [SEQ ID NO:31] | 75 | 100 | 5 | 5 | 5 | 5 | 2.5 | — |
| RWWR-OMe [SEQ ID NO:32] | >200 | >200 | =200 | 100/200 | 100 | 200 | 20 | 20 |

[a]Concentration series: 200, 100, 75, 50, 25, 10, 5 and 2.5 µg/ml.
[b]Capital letters represent L-amino acids, non-capital letters represent D-amino acids

TABLE 5

Antibacterial activity of short peptide derivatives
Values are given as MIC (MBC) values in µg/ml.

| Peptide[a] | E. coli | S. aureus | MRSA[b] | MRSE[c] |
|---|---|---|---|---|
| Dipeptides | | | | |
| RW OBz | >200 (>200) | 50 (50) | 25 (50) | 20 (20) |
| rw OBz | >200 (>200) | 50 (75) | 50 (75) | 20 (25) |
| RW DaeZ | >200 (>200) | 50 (75) | | |
| Ind RW OBz | >200 (>200) | 20 (20) | | |
| Chx RW OBz | 200 (>200) | 75 (75) | | |
| Ind RW DaeZ | >200 (>200) | 75 (75) | | |
| WR OMe | >200 (>200) | >200 (>200) | >200 (>200) | >200 (>200) |
| Ind WR OMe | >200 (>200) | >200 (>200) | | |
| Chx WR OMe | >200 (>200) | >200 (>200) | | |
| Tripeptides | | | | |
| WRW OBz | 75 (200) | 5 (5) | 5 (10) | 5 (5) |
| wrw OBz | 75 (200) | 5 (5) | 5 (10) | 5 (5) |
| wRW OBz | 75 (100) | 20 (20) | 20 (20) | 10 (10) |
| WWR OMe | >200 (>200) | >200 (>200) | >200 (>200) | >200 (>200) |
| RWR OMe | >200 (>200) | >200 (>200) | >200 (>200) | 100 (200) |
| Tetrapeptides | | | | |
| RWRW OBz [SEQ ID NO:33] | 75 (100) | 5 (5–10) | 5 (5–10) | 2.5 (2.5) |
| RWrw OBz [SEQ ID NO:34] | 75 (75–100) | 5 (5) | 2.5–5 (5) | 2.5 (2.5) |
| RWWR OMe [SEQ ID NO:32] | >200 (>200) | 75 (100–200) | 50 (100–200) | 20 (20) |
| Super bulky | | | | |
| TbtR OMe | 25 (200) | 10 (10) | | |
| RTbtR OMe | 25 (50) | 5 (5) | | |

[a]Capital letters represent L-amino acids, non-capital letters represent D-amino acids.
[b]MRSA is Methicillin resistant S. aureus.
[c]MRSE is Methicillin resistant S. epidermidis.
Titer series: 200, 100, 75, 50, 25, 10, 5, 2.5 µg/ml With the exception of the two peptides containing Tbt, none of the peptides of Examples 1 or 2 displayed measurable haemolysis (i.e. EC50>1000 µg/ml). The dipeptide Tbt-Arg-OMe had an EC50 of 360 µg/ml but surprisingly the tripeptide Arg-Tbt-Arg-OMe was less toxic with an EC50 of 720 µg/ml, despite its higher activity against both E. coli and S. aureus.

Although arginine is preferred, lysine can be used without significant loss of antibacterial activity. Phenylalanine, due to its smaller size is less active than tryptophan.

Example 3

The peptide Arg-(2-Nal)-Arg-Tyr-Arg-(2-Nal)NH$_2$ [SEQ ID NO:35] wherein (2-Nal) is 2-naphtylalanine was prepared and tested against a range of clinically important pathogens as shown in Table 6 below.

The peptide was synthesised on a 9050 Millipore Automatic Peptide Synthesizer using Fmoc protection and activation with pentafluorophenyl (Pfp)esters or in situ activation with the coupling reagent HATU (O-(7-azabenzotriazol-1-yl)-1,1,3,3-tetramethyl uronium hexafluorophosphate). In the case of coupling with pentafluorophenyl esters, 1-HOBt (1-hydroxy-benzotriazole) was added to catalyse the reaction, and when using the coupling reagent HATU the reaction was base catalysed with DIPEA (diisopropylethylamine). All amino acids with reactive side chains were protected with acid labile protecting groups and cleaved upon treatment with TFA (trifluoroacetic acid) containing scavengers. (See below for scavenger mixture). At the same time the peptide was cleaved from the solid support on treatment with the TFA solution.

A) Attachment of the First Amino Acid to the Solid Support

The solid support PAC-PEG-PS (Peptide Acid-Poly Ethylene Glycol-Poly Styrene resin) (1 eq.) was mixed together with Fmoc-(2-Nal)-OPfp (5 eq.) and DMAP (dimethylaminopyridine) (1 eq.) in a small volume of DMF (dimethylformamide) and left to swell for 30 minutes. The solution was then stirred slowly for 4½ hours. Ac$_2$O (acetic acid anhydride) (2.5 eq.) and DMAP (0.1 eq.) were then added to the solution in order to acetylate any remaining hydroxyl groups on the solid support. The solution was then stirred for another hour. The solid support with the C-terminal amino acid attached was isolated by filtration and washed several times on the filter with DMF. The solid support was then used in the synthesis of the target peptide on the 9050 Millipore Automatic Peptide Synthesizer.

B) Ninhydrin Test/Kaiser's Test

Less than 1 mg of the peptide-resin complex was treated with small equal volumes of a 5% ninhydrin solution in ethanol, a solution of 80 g phenol in 20 ml ethanol and a solution of dried, distilled pyridine. The reaction mixture was heated for two minutes at 110° C., and investigated under a microscope. (In this test a yellow reaction mixture indicates successful acetylation, while a blue solution indicates still free amino groups.)

C) Cleavage of Acid Labile Protecting Groups

Cleavage of acid labile protection groups and cleavage of the peptides from the solid support was achieved using a mixture of 2% anisol, 2% ethandithiol (EDT), 2% water and 2% phenol in TFA, and with cleavage times of no more than four hours. The solid support was then removed by filtration and the peptide precipitated in diethyl ether. The ether solution containing TFA was removed using a pasteur pipette, and the peptide was washed several times with diethylether and dried under high vacuum.

D) Purification

The peptide was purified by HPLC using a C18-reversed phase column (*) and a mixture of water and acetonitrile (both added 0.1% TFA) as mobile phase. Selected wavelength for detection of peptide fractions was 254 nm.

(*) PrePak™Cartridge 25×100 mm. DeltaPak™ C18 15 μm 100 Å. (waters corporation.)

E) Analysis

The peptide was analysed for impurities on an analytical HPLC C18-reversed phase column using a mixture of water and acetonitrile (both added 0.1% TFA) as mobile phase. The molecular weight of the peptides were determined by positive ion electrospray ionization mass spectrometry (VG Quattro Quadrupole).

Amino Acid Derivatives Used in Synthesis Selected from the Following

| | |
|---|---|
| Fmoc-AlaPEG-PS (solid support) | Fmoc-Lys(tBoc)-OPfp |
| Fmoc-Arg(Pbf)-OH | Fmoc-Met-OPfp |
| Fmoc-Arg(Pmc)-OH | Fmoc-β-(2-naphthyl)-alanine-OH |
| Fmoc-Asn(Trt)-OPfp | Fmoc-Phe-OPfp |
| Fmoc-Cys(Acm)-OPfp | Fmoc-Ser(tBu)-OPfp |
| Fmoc-Gln-OPfp | Fmoc-Thr(tBu)-OPfp |
| Fmoc-Glu(OtBu)-OPfp | Fmoc-Trp-OPfp |
| Fmoc-Gly-OPfpFmoc-Tyr(tBu)-OPfp | Fmoc-Leu-OPfp |
| Fmoc-(2-Nal)-OPfp | |

Amino acid derivatives were purchased from either Bachem, MilliGen/Biosearch (Division of Millipore) or PerSeptive Biosystems.

TABLE 6

| Pathogen | MIC (μg/ml) | MBC (μg/ml) |
|---|---|---|
| E. coli | 10 | 15 |
| S. aureus | 5 | 5 |
| MRSA | 2.5 | 5 |
| MRSE | 2.5 | 2.5 |

MRSA = Methicillin resistant S. aureus
MRSE = Methicillin resistant S. epidermidis Example 4

A further series of peptides was designed and made to investigate the impact of different sized bulky and lipophilic groups and their relative position with the molecule.

Most of the following peptides were made from the same starting material, ROBzl. A method was developed for the manufacture of ROBzl from BocR by the following 2 step method:

From the RoBzl starting material, the peptides were made using the standard two step protocol with amide bond formation and deprotection of the N-terminus.

In order to test the 'super bulky' group, i.e. peptides having only one very large bulky and lipophilic group, dipeptide methyl esters (XROMe) were prepared. By way of example, the synthesis of TbtR OMe is described in Example 2 above. Analogous methods were used in the preparation of the other methyl esters.

The antibacterial activity of the various peptides measured as MIC in μg/ml is shown in Table 7 below.

TABLE 7

| | | Antibacterial activity measured as MIC in μg/ml. | | | | |
|---|---|---|---|---|---|---|
| Class | Peptide | E. coli μg/ml | S. aureus μg/ml | MRSA μg/ml | MRSE μg/ml | P. aerug. μg/ml |
| OBzl | tBuGR-OBzl | >300.0 | >300.0 | 100.0 | 150.0 | >300.0 |
| | tBuAR-OBzl | >300.0 | 300.0 | 150–200 | 100.0 | >300.0 |
| | ChxAR-OBzl | 300.0 | 50–100 | 25–37.5 | 25.0 | >300.0 |
| | FR-OBzl | >300.0 | >300.0 | 25–37.5 | 100.0 | >300.0 |
| | RF-OBzl | >300.0 | 300.0 | 150.0 | 100.0 | |
| | WR-OBzl | >300.0 | 100.0 | 37.5 | 50.0 | >300.0 |
| | RW-OBzl | >300.0 | 100.0 | 50.0 | 25.0 | |
| | tBuFR-OBzl | 200.0 | 25.0 | 12.5–25 | 5.0 | 100.0 |
| | BipR-OBzl | 150.0 | 5.0 | 5.0 | 5.0 | 100.0 |
| OMe | WR-OMe | >500.0 | >500.0 | >500.0 | >500.0 | |
| | RW-OMe | >300.0 | >300.0 | >300.0 | 200.0 | |
| | tBuFR-OMe | >300.0 | >300.0 | 100.0 | 100.0 | >300.0 |
| | BipR-OMe | >300.0 | 150.0 | 50.0 | 50.0 | >300.0 |
| | TbtROMe | 30.0 | 4.0 | 4.0 | 4.0 | |

Titre series: 500, 300, 200, 150, 100, 50, 50, 37.5, 30, 25, 12.5, 5, 4, 2 and 1.

None of these peptides had measurable toxicity against red blood cells.

Example 5

A further group of hexapeptides and tetrapeptides were prepared on a solid phase multiple peptide synthesizer MBS 396 as described in previous examples. These were tested against *E. coli* and *S. aureus* and their minimum inhibitory concentrations (MIC) are given in Table 8 below. The first column is the value in μg/ml and the second in μM/ml. Alanine residues are included as 'spacers' and to investigate the impact of length on activity.

TABLE 8

| Peptide | *E. coli* | | *S. aureus* | |
|---|---|---|---|---|
| AAWWRR-NH2 Pmc+ [SEQ ID NO:36]; | 20 | 18.0 | 2.5 | 2.3 |
| RRAAWW-NH2 Pmc+ [SEQ ID NO:37]; | 20 | 18.0 | 2.5 | 2.3 |
| AWRWRA-NH2 Pmc+ [SEQ ID NO:38]; | 20 | 18.0 | 2.5 | 2.3 |
| WRAAWR-NH2 Pmc+ [SEQ ID NO:39]; | 50 | 45.0 | 2.5 | 2.3 |
| WWAARR-NH2 Pmc+ [SEQ ID NO:40]; | 50 | 45.0 | 5 | 4.5 |
| WWAARR-NH2 [SEQ ID NO:41]; | >200 | 237.0 | >200 | 237.0 |
| AAWWRR-NH2 [SEQ ID NO:42]; | >200 | 237.0 | >200 | 237.0 |
| RRAAWW-NH2 [SEQ ID NO:43]; | >200 | 237.0 | >200 | 237.0 |
| WRAAWR-NH2 [SEQ ID NO:44]; | >200 | 237.0 | >200 | 237.0 |
| AWRWRA-NH2 [SEQ ID NO:45] | >200 | 237.0 | >200 | 237.0 |
| BBRR-NH2 [SEQ ID NO:46]; | 50 | 64.4 | 5 | 6.4 |
| WBRR-NH2 Pmc+ [SEQ ID NO:47]; | >100 | 99.5 | 5–10 | 5.0–9.9 |
| WBRR-NH2 [SEQ ID NO:48] | >100 | 135.3 | 20 | 27.1 |
| BBRRAA-NH2 [SEQ ID NO:49]; | 75 | 81.7 | 5 | 5.4 |
| AABBRR-NH2 [SEQ ID NO:50]; | 20–35 | 21.8–38.1 | 5 | 5.4 |
| BBAARR-NH2 [SEQ ID NO:51]; | >150 | 163.4 | 5 | 5.4 |
| AAWBRR-NH2 [SEQ ID NO:52]; | 150 | 170.2 | 20–35 | 22.7–39.7 |
| WBAARR-NH2 [SEQ ID NO:53]; | >300 | 340.5 | 35 | 39.7 |
| WBRRAA-NH2 [SEQ ID NO:54]; | >300 | 340.5 | 75 | 85.1 |
| AWRBRA-NH2 Pmc+ [SEQ ID NO:55]; | 10 | 8.7 | 2.5 | 2.2 |
| AAWRBR-NH2 Pmc+ [SEQ ID NO:56]; | 15 | 13.1 | 2.5 | 2.2 |
| RRAAWW-NH2 Pmc+ [SEQ ID NO:57]; | 20 | 17.4 | 2.5 | 2.2 |
| WRBRAA-NH2 Pmc+ [SEQ ID NO:58]; | 15 | 13.1 | 5 | 4.4 |
| RRAAWB-NH2 [SEQ ID NO:59]; | 150–300 | 170.2–340.5 | 10 | 11.3 |
| AWRBRA-NH2 [SEQ ID NO:60]; | 35 | 39.7 | 35 | 39.7 |
| WRAABR-NH2 [SEQ ID NO:61]; | 150 | 170.2 | 35 | 39.7 |
| WRBRAA-NH2 [SEQ ID NO:62]; | 150 | 170.2 | 35 | 39.7 |
| AAWRBR-NH2 [SEQ ID NO:63] | 150–300 | 170.2–340.5 | 35 | 39.7 |

B = biphenylalanine

This data shows excellent activity, particularly for those peptides having the super bulky Pmc group against the Gram positive bacteria. The data also shows the actual sequence is not highly significant. Surprisingly and advantageously, the smaller peptides are more active and advantageously, c.f. WBRR [SEQ ID NO:48] and WBRRAA. [SEQ ID NO:54]

Example 6

Described below are general procedures for peptide coupling, deprotection and purification as used, or suitable for use, in preparing the peptides described herein.

Peptide Coupling General Procedure

Synthesis

The N-Boc protected amino acid derivative (1.05 eq) and C-terminal protected (either as methyl ester, benzyl ester, biphenylmethyl ester or beta-naphtyl amide) amino acid derivative (1.00 eq) and 1-hydroxybenzotriazole (HOBT) (1.2 eq) were added to the reaction vessel. Diisopropylethylamine (DIPEA) (2.4 eq) and dimethyl-formamide (DMF) (5 ml/mmol N-Boc protected amino acid) was added. The reaction mixture was stirred until all components were dissolved. O-(Benzotriazol-1-yl)-N,N,N',N'-tetramethyluronium hexafluorophosphate (HBTU) (1.2 eq) was added portionwise. The reaction mixture was shaken for 1 h.

Extraction and Work-Up

The reaction mixture from a 1 mmol batch was diluted with ethyl acetate (16 ml) and washed twice with a mixture of 12 ml 5% citric acid and 5 ml brine. The subsequent organic phase was washed twice with a mixture of 6 ml saturated sodium bicarbonate and 2 ml brine.

Cleavage of the N-Boc Protected Peptide

A suitable procedure is described earlier in these Examples.

Purification and Analysis of the Peptides

The peptides were purified on an RP-HPLC C18-column (Delta-Pak C18, 100 Å, 15 μm, 25×100 mm, Waters Corporation, Milford, Mass., USA) using a mixture of water and acetonitrile (containing 0.1 TFA) as mobile phase and employing UV-detection at 254 nm. All peptides were analyzed for impurities on an analytical RP-HPLC C18-column (Delta-Pak C18, 100 Å, 5 μm, 3.9×150 mm, Waters Corporation) with a mixture of water and acetonitrile (containing 0.1% TFA) as mobile phase. Purity of all peptides was found to be above 96%. The integrity of the peptides was checked by positive ion electrospray ionization mass spectrometry on a VG Quattro quadrupole mass spectrometer (VG Instruments Inc., UK).

Example 7

Preparation of H-Arg-OBzl (after Bodanszky, M and Bodanszky, A, "The practice of peptide synthesis" (1994) Springer Verlag, p. 30-31)

Water (2 ml) was added to a solution of Boc-Arg-OH (2.5 mmol) in methanol (20 ml). The solution was neutralised with a 20% solution of $Cs_2CO_3$ in water and then evaporated in vacuo to dryness. Residual water was removed by repeated addition and evaporation of toluene. The solid cesium salt of Boc-arginine was treated with DMF (25 ml) and benzyl bromide (3 mmol) and stirred at room temperature for 6 h. The DMF was removed in vacuo and the product was dissolved in acetone and filtered. The filtrate was evaporated in vacuo and the product was treated with 95% trifluoroactetic acid (TFA) (4 ml). The resulting product H-Arg-OBzl was isolated by tituration by diethyl ether.

The salt of H-Arg-OBzl was isolated by treating the product with para-toluenesulfonic acid (5 mmol) in ether.

Preparation of H-Arg-OBip (after Bodanszky, M and Bodanszky, A, "The practice of peptide synthesis" (1994) Springer Verlag, p. 30-31)

Water (2 ml) was added to a solution of Boc-Arg-OH (2.5 mmol) in methanol (20 ml). The solution was neutralised with a 20% solution of $Cs_2CO_3$ in water and then evaporated in vacuo to dryness. Residual water was removed by repeated addition and evaporation of toluene. The solid cesium salt of Boc-arginine was treated with DMF (25 ml), biphenylmethylchloride (3 mmol) and potassium iodide (1 mmol) and stirred at room temperature for 6 h. The DMF was removed in vacuo and the product was dissolved in acetone and filtered. The filtrate was evaporated in vacuo and the product was treated with 95% trifluoroactetic acid (TFA) (4 ml). The resulting product H-Arg-OBip was isolated by tituration by diethyl ether. The salt of H-Arg-OBip was isolated by treating the product with para-toluenesulfonic acid (5 mmol) in ether.

Example 8

The following C terminally modified dipeptides were also made and tested. For convenience, their chemical structures are given below

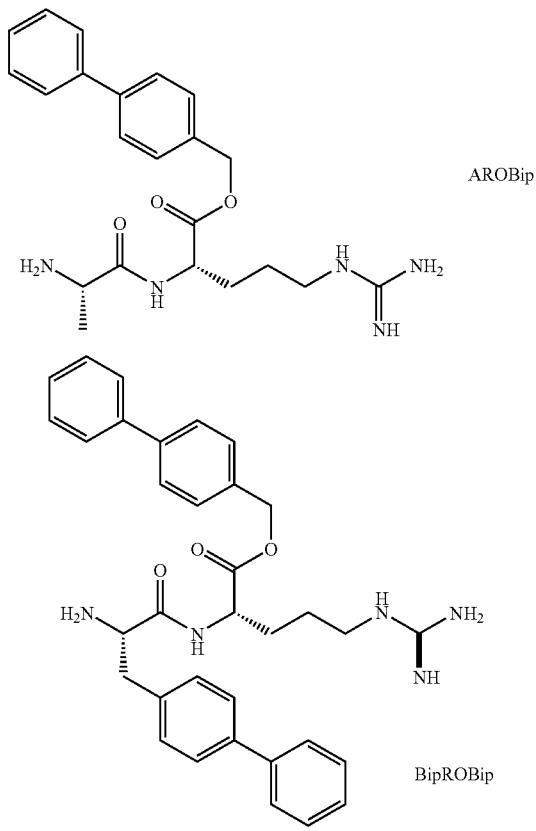

AROBip

BipROBip

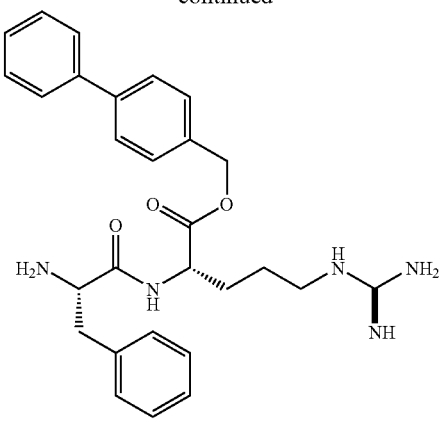

FROBip

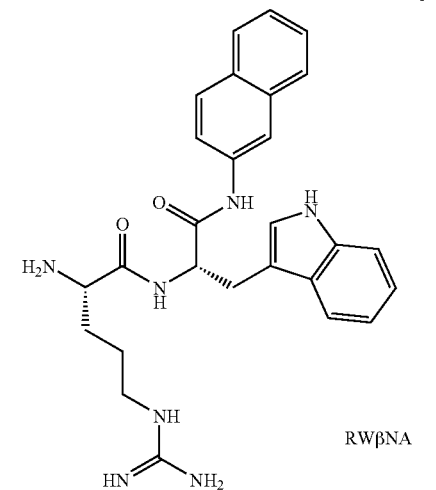

RWβNA

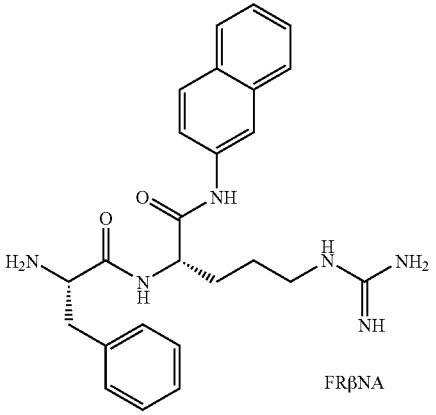

FRβNA

TABLE 9

| | Minimum inhibitory concentrations in μg/ml | | | | |
|---|---|---|---|---|---|
| Peptide | E. coli | S. aureus | P. aeruginosa | MRSA | MRSE |
| AROBip | 300 | 100 | | 37.5 | 25 |
| FROBip | 100 | 12.5 | | 12.5 | 5 |
| BipROBip | 50 | 5.0 | | 5.0 | 5.0 |
| FRβNA | >150 | 5 | >300 | 12.5 | 5 |
| RWβNA | 100 | 12.5 | | 12.5 | 12.5 |

βNA = beta-naphtylamine

Example 9

Peptidomimetics based on KWOBzl have been prepared and tested to demonstrate that a peptide structure is not required for activity, provided the desired structural motifs are present.

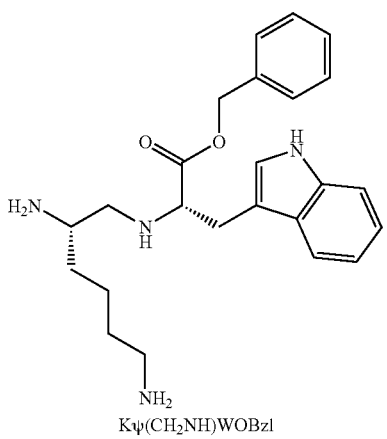

Kψ(CH₂NH)WOBzl

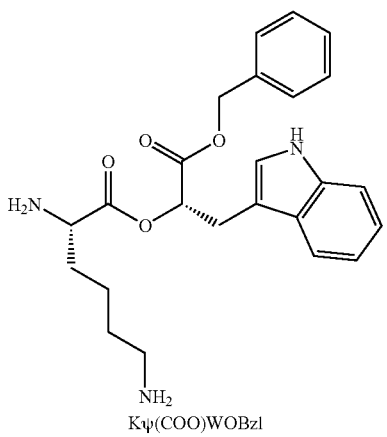

Kψ(COO)WOBzl

The first compound was obtained from Neosystems in France. The second compound was prepared from indoleacetic acid using standard techniques (Cs salt mediated esterification of the acid with benzyl bromide) ane coupling to diBoc lysine using a standard coupling protocol.

These results indicate that the ester derivatives are at least as active as their peptide equivalents and illustrates the benefits of a carbonyl group.

Example 10

The following diphenylethylene diamines available from the Aldrich catalogue were also tested and all had a MIC value against *S. aureus* of 250 µg/ml.

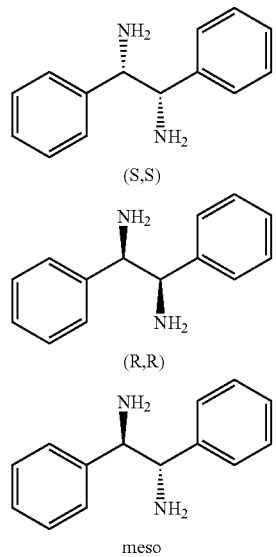

Example 11

The following molecules consisting of a modified single super bulky amino acid were made and tested for their antimicrobial activity.

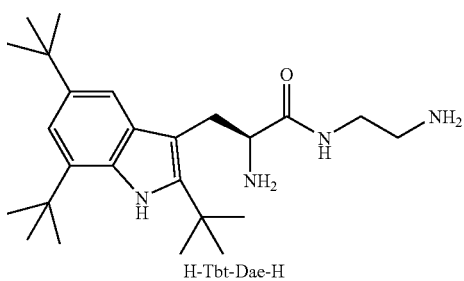

H-Tbt-Dae-H

TABLE 10

Minimum inhibitory concentrations in µg/ml

| Peptide | E. coli | P. aeruginosa | S. aureus | MRSA | MRSE |
|---|---|---|---|---|---|
| KW-OBzl | >300 | | 37.5 | 37.5 | 25 |
| kW-OBzl | >300 | | 100 | | |
| Kψ(CH₂NH)WOBzl | >300 | | 300 | | |
| Kψ(COO)WOBzl | 150 | 300 | 50 | 100 | 37.5 |
| Kψ(COO)wOBzl | 150 | 300 | 50 | 100 | 37.5 |

Lower case letters denote D-enantiomers

-continued

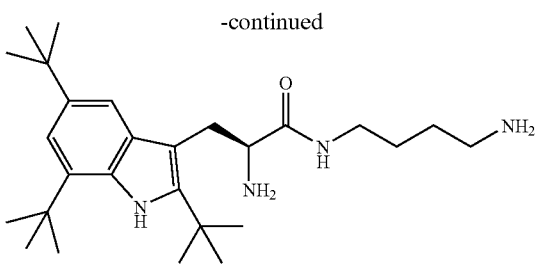

H-Tbt-Dab-H

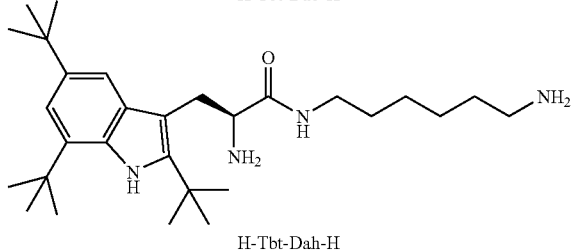

H-Tbt-Dah-H

Boc-Tbt-Dab-Z:

A mixture of Boc-Tbt-OH (0.7510 g, 1.6 mmol), N-Z-1,4-diaminobutane mono-hydrochloride (0.4323 g, 1.7 mmol), HOBt (0.8715 g, 5.7 mmol), DIPEA (1.63 ml, 9.5 mmol) in 12 ml DMF/CH$_2$Cl$_2$ (1:1) is stirred in an ice/water bath and HBTU (0.7220 g, 1.9 mmol) is added in small portions over 10 min. The mixture is stirred for another 30 min, the cooling bath is removed and stirring is continued for 2 hrs and 30 min. The reaction mixture is evaporated in vacuo. The resulting liquid oil is dissolved in dichloro-methane and subsequently extracted 3×5 ml saturated NaHCO$_3$, 2×5 ml 10% citric acid, 10 ml water and 5 ml saturated NaCl, before it was dried over MgSO$_4$ and evaporated to an light yellow oil. The oil is triturated with water and dried in vacuo. Purification of the crude product by flash chromatography (6% MeOH—CHCl$_3$) afforded 0.96 g (89%) of the title compound.

Boc-Tbt-Dae-Z and Boc-Tbt-Dah-Z were prepared by the same procedure as described for Boc-Tbt-Dab-Z. Crude products were obtained in almost quantitative yield, and purification by flash chromatography was not necessary.

Removal of the Z-protecting group was performed by over night hydrogenation (1 atm) over 10% Pd on charcoal in methanol/water (19:1). The catalyst was removed by filtration through Celite. Evaporation of the solvent in vacuo afforded the free amine as an yellow oil. The Boc-protecting group was removed by treatment with Reagent K. The deprotected Boc-diamine was isolated as a white solid by treating the oily residue after evaporation of the reaction mixture in vacuo with p-toluensulfonic acid in diethyl ether. The crude products were purified by RP-HPLC, and lyophilized to white powders.

TABLE 11

Antimicrobial activity (as MIC in µg/ml) of Tbt-diamine amides

| Compound | MIC E. coli | MIC S. aureus |
|---|---|---|
| H-Tbt-Dae-H | 15 | 15 |
| H-Tbt-Dab-H | 35 | 35 |
| H-Tbt-Dah-H | 15 | 15 |

Tbt: β-(2,5,7-tri-tert-butylindol-3-yl)alanine
Dae: 1,2-diaminoethane
Dab: 1,4-diaminobutane
Dah: 1,6-diaminohexane Example 12

Several original structures, embodying the combination of a bulky lipophilic group and a polar residue, can be easily accessed from cheap raw material such as cyclopentadiene. Two such compounds are shown below, already demonstrating the versatility of the cyclopentane-based scaffold. Indeed, a simple change in the order of addition of the bulky or the polar groups leads to two different products 1 and 2.

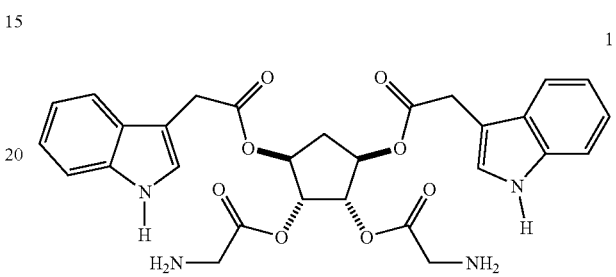

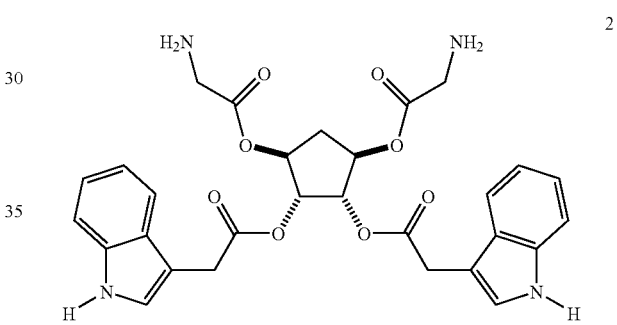

The synthetic route followed for the preparation of compound 1, and applicable to the preparation of 2, is depicted below.

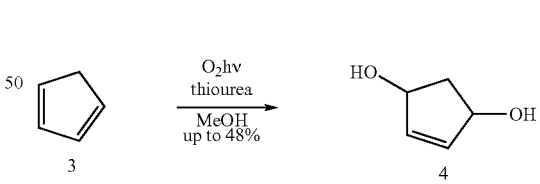

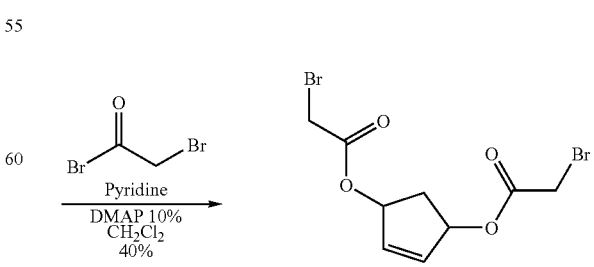

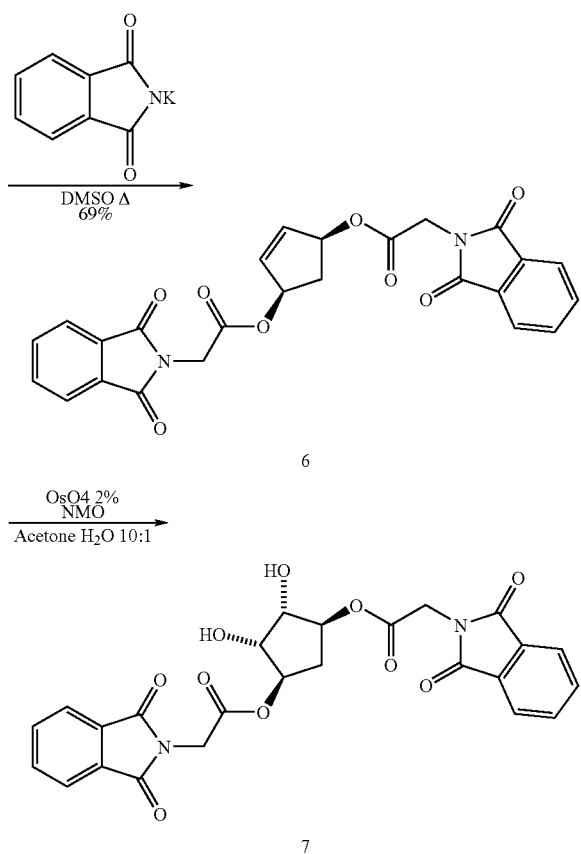

Cyclopentadiene 3 was reacted with singlet oxygen, generated in situ by photolysis of oxygen in the presence of rose bengale as the photosensitiser, affording the corresponding endoperoxide. This peroxide was not isolated but reduced directly by the thiourea present in the reaction mixture, into the desired cis-diol 4 in an overall yield of 48%. Esterification of the cis-diol 4 using an excess of bromoacetyl bromide in the presence of pyridine and DMAP afforded the desired diester 5 in 40% yield. The subsequent transformation of diester 5 into the advanced intermtiediate 6 was smoothly accomplished by nucleophilic substitution using the potassium anion of phthalimide. Alkene 6 was then dihydroxylated from the α-face under classical osmium-catalysed conditions, leading to the desired diol 7 in essentially quantitative yield. The conversion of diol 7 into the final product 1 was effected by DCC-mediated coupling of 7 with indole carboxylic acid followed by deprotection of the phthaimido protecting group by hydrazine hydrate in hot ethanol. The inverse sequence was followed to prepare 2.

This versatile sequence can be transposed to the preparation of a variety of analogues by modifying the order of the addition of the bulky and polar functions, by altering the relative stereochemistry of the four hydroxyl functions substituting the cyclopentane skeleton and by changing the size and nature of the bulky and polar groups. This strategy is illustrated by some structures shown below but this is by no means an exhaustive list.

P = polar group; B = bulky group

Experimental Procedures 1,3-dihydroxy-4-cyclopentene preparation

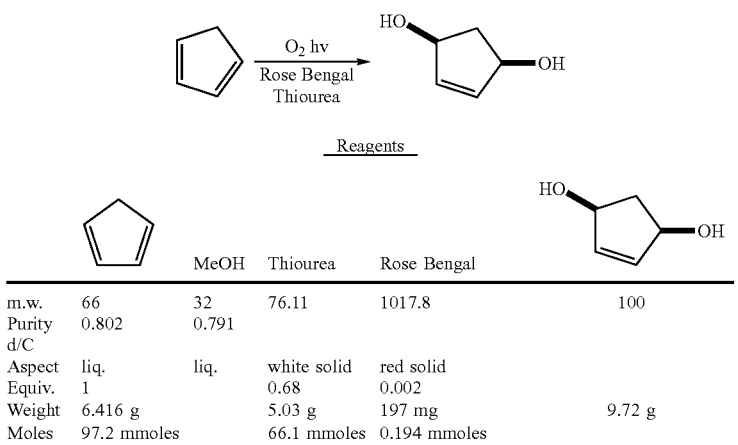

| | | MeOH | Thiourea | Rose Bengal | |
|---|---|---|---|---|---|
| m.w. | 66 | 32 | 76.11 | 1017.8 | 100 |
| Purity d/C | 0.802 | 0.791 | | | |
| Aspect | liq. | liq. | white solid | red solid | |
| Equiv. | 1 | | 0.68 | 0.002 | |
| Weight | 6.416 g | | 5.03 g | 197 mg | 9.72 g |
| Moles | 97.2 mmoles | | 66.1 mmoles | 0.194 mmoles | |

Reagents

|  | | MeOH | Thiourea | Rose Bengal | |
|---|---|---|---|---|---|
| Vol. | 8 ml | 1.81 | | | |
| Formula | $C_5H_6$ | $CH_3OH$ | $CSN_2H_4$ | $C_{20}H_2Cl_4I_4Na_2O_5$ | |
| b.p. | 43° C. | 65° C. | | | |

To a solution of thiourea (5.03 g; 0.68 eq.) and Rose Bengal (197 mg; 0.002 eq.) in distilled methanol (1.81) was added 8 ml of freshly distilled cyclopentadiene (1 eq.) at 0° C. Oxygen was passed through the solution. After 2 h, it was irradiated with a 450 W mercury lamp and the flux of oxygen was maintained over 2 h. Then, the solution was kept in the dark and the oxygen was turned off overnight. The mixture was concentrated to 200 ml and filtrated through charcoal and Celite® several times until it was colorless. Then, it was dried on $Na_2SO_4$ and the solvent was removed under reduce pressure without heating. The crude product was purified by horizontal distillation (115° C., $10^{-4}$ mbar) to obtain 3,525 g (36% yield) of a yellow low melting point solid.

NMR $H^1$ DMSO 300 MHz δ in ppm (multiplicity): 1.53 (dt); 2.82 (dt); 4.67(d); 5.16 (s); 6.03 (s)

Dibromo-Diester Preparation

Reagents

|  |  | Bromoacetic bromide | Pyridine | DMAP | DCM | Product |
|---|---|---|---|---|---|---|
| m.w. | 100 | 202 | 79 | 122.12 | | 341 |
| Purity | | | | | | |
| d/C | | 2.317 | 0.978 | | 1.325 | |
| Aspect | Yellow liq. | liq. | liq. | white solid | | |
| Equiv. | 1 | 3 | 3 | 0.08 | | |
| Weight | 7.05 g | 42.622 g | 16.67 g | 0.7 g | | |
| Moles | 70.5 mmoles | 211 mmoles | 211 mmoles | 5.7 mmoles | | 24.04 g |
| Vol. | | 18.39 ml | 17.04 ml | | 106 ml | |
| Formula | $C_5H_8O_2$ | $C_2H_2Br_2O$ | $C_5H_6N$ | $C_7H_{10}N_2$ | $CH_2Cl_2$ | |
| b.p. | 115° C. ($10^{-4}$ mbar) | 147° C. | 115° C. | | 40.° C. | |

To a solution of 7.05 g (1 eq.) of diol and 46.62 g (3 eq.) of bromoacetic bromide in 250 ml of dichloromethane was added 17.04 ml (3 eq.) of pyridine and 700 mg (0.08 eq.) of DMAP at 0° C. The solution was allowed to warm to room temperature and was maintained under agitation overnight. Then, 700 ml of DCM were added and the organic phase was washed with 70 ml of 3M HCl, 140 ml of a saturated solution of NaHCO$_3$ and 140 ml of water. The organic layer was dried on Na$_2$SO$_4$, filtrated and the solvent was remove under reduce pressure. The crude product was purified by a Flash chromatography (AcOEt/EP 35:75) to obtain 9.76 g (40.6% yield) of a colorless liquid.

NMR H$^1$ CDCl$_3$ 300 MHz δ in ppm (multiplicity): 1.8 (dt); 2.89 (dt); 3.91 (s); 5.58 (dd); 6.13 (s)

Diphtalimido-Diester Preparation

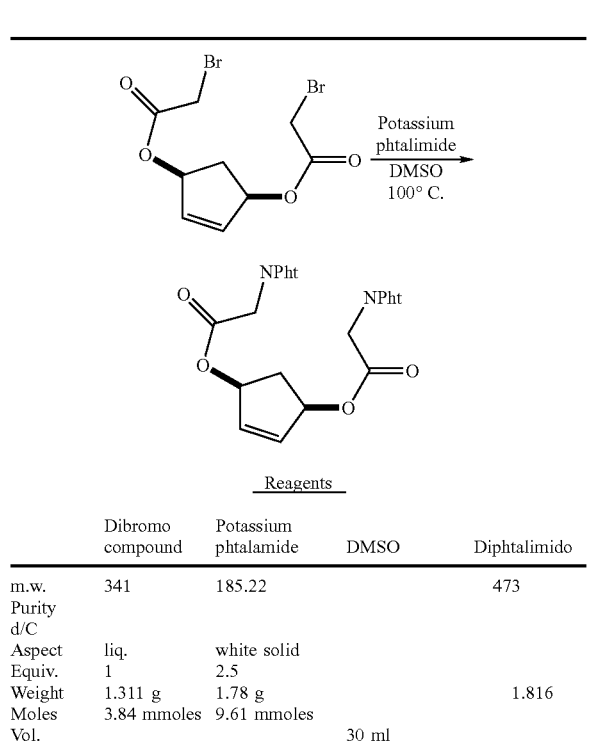

Reagents

|  | Dibromo compound | Potassium phtalamide | DMSO | Diphtalimido |
|---|---|---|---|---|
| m.w. | 341 | 185.22 |  | 473 |
| Purity d/C |  |  |  |  |
| Aspect | liq. | white solid |  |  |
| Equiv. | 1 | 2.5 |  |  |
| Weight | 1.311 g | 1.78 g |  | 1.816 |
| Moles | 3.84 mmoles | 9.61 mmoles |  |  |
| Vol. |  |  | 30 ml |  |

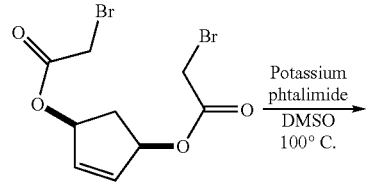

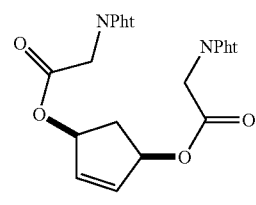

Reagents

|  | Dibromo compound | Potassium phtalamide | DMSO | Diphtalimido |
|---|---|---|---|---|
| Formula | C$_9$H$_{10}$Br$_2$O$_4$ | C$_8$H$_4$KNO$_2$ | C$_2$H$_6$SO |  |
| b.p. |  |  | 189° C. |  |

A solution of 1.311 g (1 eq.) of the dibromo compound and 1.78 g (2.5 eq.) of potassium phtalamide in 30 ml of DMSO was kept under reflux overnight. The mixture was diluted with 250 ml of diethylether and was washed 3 times by 150 ml of brine. The organic layer was dried on Na$_2$SO$_4$, filtrated and the solvent was removed under reduce pressure. The crude product was purified by a Flash chromatography (AcOEt/EP 80:20) to obtain 1.24 g (68.8% yield) of a white solid.

NMR H$^1$ CDCl$_3$ 300 MHz δ in ppm (multiplicity): 1.85 (dt) 2.87 (dt); 4.42 (s); 5.61 (dd); 6.11 (s); 7.85(m)

The invention claimed is:

1. A method of destabilizing microbial cell membranes in a patient suffering from or at risk of being affected by a microbial infection which comprises administering to said patient a molecule of 2 to 4 amino acids or equivalent subunits in length, and incorporating a bulky and lipophilic group comprising at least 11 non-hydrogen atoms and containing no more than 2 polar functional groups, wherein said bulky and lipophilic group incorporates one or more closed rings of 5 or more non-hydrogen atoms, said molecule further having at least two more cationic than anionic moieties.

2. A method as claimed in claim 1, wherein said bulky and lipophilic group comprises at least 13 non-hydrogen atoms.

3. A method as claimed in claim 1, wherein said super bulky group incorporates 2 closed rings of 5 or more non-hydrogen atoms.

4. A method as claimed in claim 1 wherein said molecule is a peptide, peptide derivative or peptidomimetic.

5. A method as claimed in claim 4, wherein said molecule comprises a modified C terminus which does not carry a negative charge.

6. A method as claimed in claim 5, wherein said C terminus is amidated or esterified.

7. A method as claimed in claim 5 or 6, wherein said modified C terminus comprises a bulky and lipophilic group.

8. A method as claimed in claim 4 wherein said peptide, peptide derivative or peptidomimetic comprises one or more amino acid or equivalent R subunits which comprises a bulky and lipophilic group.

9. A method as claimed in claim 8, wherein one or more of said amino acid or subunits comprises a cationic moiety.

* * * * *